US011651117B2

United States Patent
Kent et al.

(10) Patent No.: US 11,651,117 B2
(45) Date of Patent: May 16, 2023

(54) SYSTEM AND METHOD FOR ANAEROBIC DIGESTION PROCESS ASSESSMENT, OPTIMIZATION AND/OR CONTROL

(71) Applicant: WEnTech Solutions Inc., Fredericton (CA)

(72) Inventors: Kenneth Blair Kent, Fredericton (CA); Amir Allaf-Akbari, Fredericton (CA); Konstantin Nasartschuk, Fredericton (CA); Kevin John Shiell, Berwick (CA); Farough Motasemi, Fredericton (CA)

(73) Assignee: WEnTech Solutions Inc., Fredericton (CA)

( * ) Notice: Subject to any disclaimer, the term of this patent is extended or adjusted under 35 U.S.C. 154(b) by 648 days.

(21) Appl. No.: 16/557,125

(22) Filed: Aug. 30, 2019

(65) Prior Publication Data
US 2020/0074307 A1 Mar. 5, 2020

Related U.S. Application Data

(60) Provisional application No. 62/727,252, filed on Sep. 5, 2018.

(51) Int. Cl.
*G06F 30/20* (2020.01)
*G06F 30/27* (2020.01)
(Continued)

(52) U.S. Cl.
CPC ............... *G06F 30/20* (2020.01); *C02F 3/28* (2013.01); *G06F 30/27* (2020.01); *G06N 3/086* (2013.01);
(Continued)

(58) Field of Classification Search
None
See application file for complete search history.

(56) References Cited

U.S. PATENT DOCUMENTS 7,831,318 B2 * 11/2010 Bartee .................. G05B 13/048
703/11
7,862,992 B2 * 1/2011 Murthy .................. C12M 41/48
435/286.1
(Continued)

FOREIGN PATENT DOCUMENTS

CA 2948830 A1 11/2015
CA 2776509 C 6/2017
(Continued)

OTHER PUBLICATIONS

Gopi Krishna Kafle et al, "Comparison on batch anaerobic digestion of five different livestock manures and prediction of biochemical methane potential (BMP) using different statistical models" vol. 48, 2016, pp. 492-502. (Year: 2016).*
(Continued)

*Primary Examiner* — Akash Saxena
(74) *Attorney, Agent, or Firm* — Bereskin & Parr LLP/S.E.N.C.R.L., s.r.l.; Tony Orsi

(57) ABSTRACT

Systems and methods are described for performing at least one of assessing, optimizing and/or controlling the performance of an Anaerobic Digestion (AD) plant. The system comprises a server that provides a user interface for allowing a user to enter user inputs to define various aspects of the AD plant operation and to view results of the simulation; a database for storing the inputs used for the simulation of the anaerobic digestion plant, the inputs including feedstock inputs, AD operational inputs, and simulation criteria; and a simulation engine that can be operated in an at least one of an off-line simulation mode for generating off-line simulator predictions, a near-line simulation mode for optimizing the
(Continued)

performance of the system and an online mode for using machine learning to tune the performance of various models used in simulating the operation of the AD plant.

31 Claims, 8 Drawing Sheets

(51) Int. Cl.
    *C02F 11/04*     (2006.01)
    *C02F 3/28*     (2006.01)
    *G06N 3/126*     (2023.01)
    *G06N 20/00*     (2019.01)
    *G06N 3/086*     (2023.01)
    *G06F 119/02*     (2020.01)

(52) U.S. Cl.
    CPC .............. *G06N 3/126* (2013.01); *G06N 20/00* (2019.01); *C02F 11/04* (2013.01); *G06F 2119/02* (2020.01)

(56) References Cited

U.S. PATENT DOCUMENTS

| | | | | |
|---|---|---|---|---|
| 8,448,336 | B2* | 5/2013 | Barcelo | G03G 15/0818 492/53 |
| 8,571,689 | B2* | 10/2013 | Macharia | C12M 41/12 703/11 |
| 10,392,747 | B2* | 8/2019 | Bhat | G05B 13/0265 |
| 10,487,282 | B2* | 11/2019 | Foody | C10L 3/105 |
| 10,755,214 | B2* | 8/2020 | Apap | G06F 17/11 |
| 10,894,724 | B2* | 1/2021 | Finke | C02F 3/006 |
| 11,198,632 | B2* | 12/2021 | Wang | C02F 1/66 |
| 11,231,324 | B2* | 1/2022 | Gilliam | G01J 3/4412 |
| 11,274,054 | B2* | 3/2022 | Kadota | C12P 5/023 |
| 2010/0267122 | A1* | 10/2010 | Chinnasamy | C12P 39/00 435/257.1 |
| 2011/0245937 | A1* | 10/2011 | Rawson | C10K 1/003 703/1 |
| 2012/0064506 | A1* | 3/2012 | Stover | C12M 29/18 435/287.5 |
| 2012/0107921 | A1* | 5/2012 | Willson | C12M 41/48 47/1.4 |
| 2015/0034553 | A1* | 2/2015 | Kumar | C02F 3/28 210/85 |
| 2017/0242981 | A1* | 8/2017 | Devereux | G05B 17/02 |
| 2018/0327292 | A1* | 11/2018 | Li | C02F 1/00 |
| 2018/0370827 | A1* | 12/2018 | Kumar | C02F 3/28 |
| 2019/0050533 | A1* | 2/2019 | Brown | G16B 40/20 |
| 2020/0074307 | A1* | 3/2020 | Kent | G06N 3/006 |
| 2021/0118175 | A1* | 4/2021 | Grancharov | G06T 11/20 |
| 2021/0132556 | A1* | 5/2021 | Yamamoto | G05B 13/026 |
| 2021/0379552 | A1* | 12/2021 | Shimoni | G05B 13/042 |
| 2021/0395120 | A1* | 12/2021 | Han | C02F 3/006 |
| 2022/0098073 | A1* | 3/2022 | Xu | C02F 9/00 |
| 2022/0135928 | A1* | 5/2022 | Kim | C12M 41/48 435/289.1 |
| 2022/0228174 | A1* | 7/2022 | Rodriguez | C02F 3/28 |

FOREIGN PATENT DOCUMENTS

| | | | |
|---|---|---|---|
| CA | 3111632 A1 | 3/2020 | |
| CN | 102351391 A | 2/2012 | |
| CN | 102446314 A | 5/2012 | |
| CN | 105112112 A | 12/2015 | |
| CN | 205046076 U | 2/2016 | |
| EP | 2559750 A1 * | 2/2013 | ............ C12M 21/04 |
| EP | 3059645 A1 | 8/2016 | |
| EP | 2419385 B1 | 8/2019 | |
| ES | 2088368 A1 | 8/1996 | |
| JP | H05169100 A | 7/1993 | |
| JP | H08197097 A | 8/1996 | |
| KR | 101018886 B1 | 3/2011 | |
| WO | WO 2020261151 * | 5/2013 | |

OTHER PUBLICATIONS

Batstone, D.J., Pind, P.F. and Angelidaki, I. (2003), Kinetics of thermophilic, anaerobic oxidation of straight and branched chain butyrate and valerate. Biotechnol. Bioeng., 84: 195-204. https://doi.org/10.1002/bit.10753 (Year: 2003).*

Theuerl S, Herrmann C, Heiermann M, Grundmann P, Landwehr N, Kreidenweis U, Prochnow A. The Future Agricultural Biogas Plant in Germany: A Vision. Energies. 2019; 12(3):396. https://doi.org/10.3390/en12030396 (Year: 2019).*

Lesteur et al., "Alternative methods for determining anaerobic biodegradability: A review", Process Biochemistry, Apr. 2010, 45(4): 431-440.

Raposo et al., "Biochemical methane potential (BMP) of solid organic substrates: evaluation of anaerobic biodegradability using data from an international interlaboratory study", Journal of Chemical Technology and Biotechnology, Apr. 2011, 86(8): 1088-1098.

Tarvin et al., "The Methane Fermentation of Organic Acids and Carbohydrates", Journal of the American Chemical Society, 1934, 56(8): 1751-1755.

Raju, "Optimization of the anaerobic digestion process by substrate pretreatment and the application of NIRS", Biological and Chemical Engineering, Technical Report BCE-TR-1, Aarhus University, Denmark, May 2012, 1(1): Chapters 1-3 (39 pages).

"Anaerobic Digestion Tools and Resources", United States Environmental Protection Agency, online article, Aug. 15, 2018 <https://www.epa.gov/anaerobic-digestion/anaerobic-digestion-tools-and-resources> (2 pages).

"Biogas Production Optimizer", YARA International ASA, online product posting, Wayback Machine Feb. 2018 <https://web.archive.org/web/20180224010127/http://yara.com/products_services/industry_chemicals/biogas_production_optimizer/> (1 page).

International Search Report and Written Opinion dated Nov. 21, 2019 in International Patent Application No. PCT/CA2019/051215 (9 pages).

Dennehy et al., "Synergism and effect of high initial volatile fatty acid concentrations during food waste and pig manure anaerobic co-digestion", Waste Management, 2016, 56: 173-180.

Extended European Search Report dated May 19, 2022, issued for EP Patent Application No. 19858545.7 (13 pages).

Ma et al., "Kinetics of psychrophilic anaerobic sequencing batch reactor treating flushed dairy manure", Bioresource Technology, 2013, 131: 6-12.

Hafner et al., "Software for biogas research: Tools for measurement and prediction of methane production", SoftwareX, Jun. 2018, 7: 205-210.

Ward et al., "Optimisation of the anaerobic digestion of agricultural resources", Bioresource Technology, Apr. 11, 2008, 99: 7928-7940.

Hamawand et al., "Anaerobic Digestion and Biogas Potential: Simulation of Lab and Industrial-Scale Processes", Energies, Jan. 13, 2015, 8: 454-474.

Xie et al., "Effect of pig manure to grass silage ratio on methane production in batch anaerobic co-digestion of concentrated pig manure and grass silage", Bioresour. Technol., 2011, 102(10): 5728-5733.

Zhao et al., "Bio-energy conversion performance, biodegradability, and kinetic analysis of different fruit residues during discontinuous anaerobic digestion", Waste Management, 2016, 52: 295-301.

Rao et al., "Bioenergy conversion studies of the organic fraction of MSW: assessment of ultimate bioenergy production potential of municipal garbage", Appl. Energy, 2000, 66(1): 75-87.

"CREST Cost of Energy Models", Renewable Energy Project Finance, National Renewable Energy Laboratory (NREL)—U.S. Department of Energy, Office of Energy Efficiency and Renewable Energy, 2011 <https://web.archive.org/web/20170701103224/https://financere.nrel.gov/finance/content/crest-cost-energy-models> (2 pages).

Barchmann et al., "Expanding the flexibility of biogas plants—substrate management, schedule synthesis and economic assessment", Landtechnik, 2016, 71(6): 233-251.

* cited by examiner

SYSTEM AND METHOD FOR ANAEROBIC DIGESTION PROCESS ASSESSMENT, OPTIMIZATION AND/OR CONTROL

CROSS-REFERENCE TO RELATED APPLICATION

This application claims the benefit of U.S. Provisional Patent Application No. 62/727,252, filed Sep. 5, 2018, and the entire contents of U.S. Provisional Patent Application No. 62/727,252 is hereby incorporated by reference.

FIELD

Various embodiments are described herein that generally relate to a systematic approach for the assessment and optimization of an anaerobic digestion process of organic waste materials.

BACKGROUND

Huge amounts of agricultural and organic wastes are produced every year that can be potential resources to the world. Anaerobic digestion is one of the bioconversion pathways to manage and utilize different streams of organic wastes and produce green bio-fuels and bio-products. Anaerobic digestion is also known as a promising natural treatment option to reduce the risk of environmental pollution by volumetric reduction in which microorganisms break down organic materials and produce biogas. In fact, the use of biogas and produced methane from the anaerobic digestion process has been adopted by many industries worldwide. This process directly facilitates and lowers greenhouse gas effects by reducing the methane emissions into the atmosphere through degradation of the agricultural and organic wastes. While anaerobic digestion has received considerable popularity and commercial success in the last several years, there has been a continuing need for improvement of this process.

The anaerobic digestion process performance, the output product's quality and quantity, as well as the plant's overall efficiency and its economic viability can be significantly affected by transient variation in feedstock characteristics, feedstock flow, process conditions and the surrounding environment. In addition, the anaerobic digestion process is highly non-linear and complex, which makes controlling the process difficult and consequently reduces the efficiency.

Currently, there is no product available in the market that can assess the anaerobic digestion process in different phases from initial assessment before the installation of the plant to the operating phase. Up to this date, large and small-scale anaerobic digestion plants are operated based on the operator's experience. Most of the assessment and initial feasibility analysis of the facilities have been done manually and based on the expertise of the engineer who performs the process. However, the variation in the characteristics of different feedstocks and the technical complexity of the anaerobic digestion process make this a more challenging process. Accordingly, the current control techniques lead to inefficient use of feedstock resources, lower energy production efficiencies, and eventually lower financial viability for the project.

SUMMARY OF VARIOUS EMBODIMENTS

In accordance with one aspect of the teachings herein, there is provided a system for performing at least one of assessing, optimizing and/or controlling the performance of an Anaerobic Digestion (AD) plant, wherein the system comprises: a user interface for allowing a user to enter user inputs to define various aspects of the AD plant operation and to view results of the simulation; a database for storing inputs used for the simulation of the anaerobic digestion plant, the inputs including feedstock inputs, AD operational inputs, and simulation criteria; and a server that controls the operation of the system and generates the user interface, the server being configured to operate a simulation engine in an off-line simulation mode for generating off-line simulator predictions of the AD plant for assessing the performance of the AD plant, the simulation engine being configured to: generate a biochemical methane potential (BMP) for the AD plant by using a feedstock model and the feedstock inputs; and generate estimates of biomethane, electricity, and thermal production of the AD plant for a simulated time interval by using an AD operational model and the AD operational inputs, the feedstock inputs and the overall BMP, where the off-line simulator predictions indicate the operational performance of the AD plant and include the overall BMP, and the estimates of biomethane, electrical and thermal production of the AD plant.

In at least one embodiment, the feedstock model includes at least one steady state equation for determining an overall BMP or the feedstock model includes at least one transient sub-model for determining a cumulative methane yield.

In at least one embodiment, at least one steady state equation determines at least one of a first BMP value due to chemical oxygen demand, a second BMP value due to elemental composition (EC) and a third BMP value due to organic fraction composition, wherein the BMP values are averaged when more than one BMP value is determined.

In at least one embodiment, the at least one transient sub-model for determining a cumulative methane yield include at least one of a first order kinetic model, a Chen and Hashimoto model, a Modified Gompertz model, and a dual pooled first order kinetic model, wherein outputs of the sub-models are averaged when at least two sub-models are used to determine the cumulative methane yield.

In at least one embodiment, the AD operational model is used to generate estimates of biomethane, electricity, biofertilizer and thermal production of the AD plant by using BMP models a digester equation, a biofertilizer equation and a digestate equation based on volume of inflows and outflows of a digester of the AD plant and mass balance equations.

In at least one embodiment, the database further comprises optimization criteria and the simulation engine is further configured to operate the simulation engine in a near-line simulation mode for determining an optimal operating point to optimize the performance of the AD plant with respect to at least one goal, the optimal operating point, one or more recipes and AD plant operational settings.

In at least one embodiment, the simulation engine includes a sensitivity analysis and optimization model for performing optimization where the sensitivity analysis and optimization model includes a set of N input variables that have an influence for achieving the at least one goal, an operating value for each input variable determined from the off-line simulation and a range over which the input variables are varied to define an N-dimensional mesh where the actual optimal operating point is a global maximum or a global minimum of the N-dimensional mesh corresponding to the at least one goal.

In at least one embodiment, the at least one optimization goal comprises maximizing biogas production, maximizing electricity production, minimizing greenhouse gas emissions and minimizing feedstock leftover or a weighted combination of those options.

In at least one embodiment, the simulation engine is configured to iteratively generate a set of operating points along the mesh until the optimal operating point is found, which is one of the operating points that is closest to the actual optimal operating point or an operating point that is closest to the at least one goal when an optimization time limit is reached.

In at least one embodiment, the simulation engine is configured to use a genetic algorithm to randomly generate a first set of operating points, apply a fitness function to the set of operating points to obtain a set of results, determine a probability score for each result to indicate how likely each corresponding operating point is to being nearest to the actual optimal operating point; select a subset of the operating points that have a higher probability score, cross-mutate the selected operating points to generate a new set of operating points and repeat the applying, determining, selecting and cross-mutating steps until one of the optimal operating point is found that is closest to the actual optimal operating point or the operating point with the best result is found when optimization time limit is reached.

In at least one embodiment, the optimal operating point is sent to a plant controller that controls the operation of the AD plant, where the optimal operating point includes a recipe and operational plant settings for a given time interval of the simulation.

In at least one embodiment, the simulation engine is further configured to operate in an online simulation mode where a machine learning model is used to simulate the operation of the AD plant to generate online simulator predictions, compare the online simulator predictions to actual results from the AD plant to determine a simulation error and adjust the machine learning model, the models used for near-line simulation and the values of some of the input variables to improve simulation performance when the simulation error is larger than an error threshold.

In at least one embodiment, the simulation engine is configured to perform the off-line and near-line simulations before the next online simulation in order to provide the online simulator with an updated optimal operating point for online simulation.

In at least one embodiment, the simulation engine is further configured to operate in an online simulation mode where a machine learning model is used to simulate the operation of the AD plant to generate online simulator predictions, compare the online simulator predictions to actual results from the AD plant and to send the plant controller subsequent recipes for the optimal operation of the AD plant for subsequent time intervals.

In another aspect, in accordance with the teachings herein, there is provided a method for performing at least one of assessing, optimizing and/or controlling the performance of an Anaerobic Digestion (AD) plant, wherein the method comprises using a server to provide a user interface for allowing a user to enter user inputs to define various aspects of the AD plant operation and to view results of the simulation; storing inputs in a database where the inputs are used for the simulation of the anaerobic digestion plant, the inputs including feedstock inputs, AD operational inputs, and simulation criteria; and using the server to generate the user interface and operate a simulation engine in an off-line simulation mode for generating off-line simulator predictions of the AD plant for assessing the performance of the AD plant by: using a feedstock model for receiving the feedstock inputs and generating an overall biochemical methane potential (BMP) for the AD plant; and using an AD operational model for receiving the AD operational inputs, the feedstock inputs and the overall BMP and generating estimates of biomethane, electricity, and thermal production of the AD plant for a simulated time interval, where the off-line simulator predictions indicate the operational performance of the AD plant and include the overall BMP, and the estimates of biomethane, electrical and thermal production of the AD plant.

In at least one embodiment, the method comprises using at least one steady state equation for determining an overall BMP or using at least one transient sub-model for determining a cumulative methane yield.

In at least one embodiment, the method further comprises determining at least one of a first BMP value due to chemical oxygen demand, a second BMP value due to elemental composition (EC) and a third BMP value due to organic fraction composition wherein the BMP values are averaged when more than one BMP value is determined.

In at least one embodiment, the method comprises determining a the cumulative methane yield by using at least one of a first order kinetic model, a Chen and Hashimoto model, a Modified Gompertz model, and a dual pooled first order kinetic model, wherein outputs of the sub-models are averaged when at least two sub-models are used to determine the cumulative methane yield.

In at least one embodiment, the method further comprises using the AD operational model to generate the estimates of biomethane, electricity, and thermal production of the AD plant by using BMP models and output models including bio-methane, electricity, bio-fertilizer, digestate and heat.

In at least one embodiment, the database further comprises optimization criteria and the method comprises operating the simulation engine in a near-line simulation mode for determining an optimal operating point to optimize the performance of the AD plant with respect to at least one goal, the optimal operating point, one or more recipes and AD plant operational settings.

In at least one embodiment, the method further comprises using a sensitivity analysis and optimization model during optimization where the sensitivity analysis and optimization model includes a set of N input variables that have an influence for achieving the at least one goal, an operating value for each input variable determined from the off-line simulation and a range over which the input variables are varied to define an N-dimensional mesh where the actual optimal operating point is a global maximum or a global minimum of the N-dimensional mesh corresponding to the at least one goal.

In at least one embodiment, the method comprises operating the simulation engine for iteratively generating a set of operating points along the mesh until the optimal operating point is found which is one of the operating points that is closest to the actual optimal operating point or an operating point that is closest to the at least one goal when an optimization time limit is reached.

In at least one embodiment, the method comprises operating the simulation engine for using a genetic algorithm to randomly generate a first set of operating points, applying a fitness function to the set of operating points to obtain a set of results, determining a probability score for each result to indicate how likely each corresponding operating point is to being nearest to the actual optimal operating point; selecting a subset of the operating points that have a higher probability score, cross-mutating the selected operating points to generate a new set of operating points and repeating the applying, determining, selecting and cross-mutating until one of the optimal operating point is found that is closest to the actual optimal operating point or the operating point with the best result is found when optimization time limit is reached.

In at least one embodiment, the method comprises sending the optimal operating point to a plant controller that controls the operation of the AD plant, where the optimal operating point includes a recipe and operational plant settings for a given time interval of the simulation.

In at least one embodiment, the method comprises operating the simulation engine in an online simulation mode where a machine learning model is used for simulating the operation of the AD plant to generate online simulator predictions, the online simulator predictions are compared to actual results from the AD plant to determine a simulation error and adjusting the machine learning model, the models used for near-line simulation and the values of some of the input variables to improve simulation performance when the simulation error is larger than an error threshold.

In at least one embodiment, the method comprises operating the simulation engine for performing the off-line and near-line simulations before the next online simulation in order to provide the online simulator with an updated optimal operating point for online simulation.

In at least one embodiment, the method comprises operating the simulation engine in an online simulation mode where a machine learning model is used for simulating the operation of the AD plant to generate online simulator predictions, comparing the online simulator predictions to actual results from the AD plant and sending the plant controller subsequent recipes for the optimal operation of the AD plant for subsequent time intervals.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1:
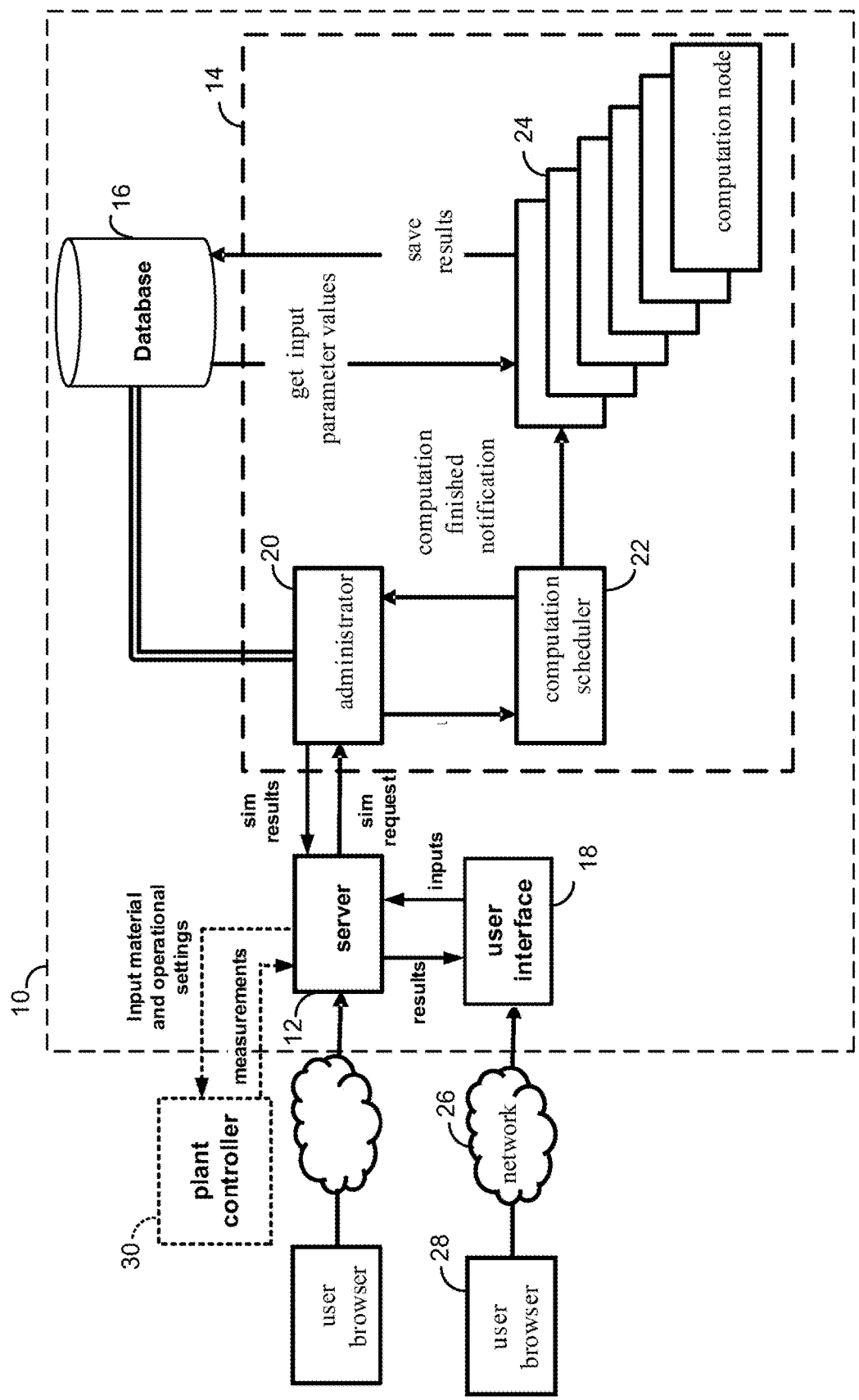
FIG. 1 is a block diagram of an example embodiment of a system for performing at least one of assessing, optimizing, monitoring and optionally controlling the operation of an Anaerobic Digestion (AD) plant that employs an anaerobic digestion process.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending on the context in which these terms are used. For example, the terms coupled or coupling can have a mechanical, fluidic or electrical connotation. For example, as used herein, the terms coupled or coupling can indicate that two elements or devices can be directly connected to one another or connected to one another through one or more intermediate elements or devices via an electrical signal, electrical connection, a mechanical element, a fluid or a fluid transport pathway depending on the particular context.

It should also be noted that, as used herein, the wording "and/or" is intended to represent an inclusive-or. That is, "X and/or Y" is intended to mean X or Y or both, for example.

As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

It should be noted that the example embodiments described in accordance with the teachings herein may be implemented as a combination of hardware and software. For example, a portion of the embodiments described herein may be implemented, at least in part, by using one or more computer programs, executing on one or more programmable devices comprising at least one processing element, and at least one data storage element (including volatile and non-volatile memory). These devices may also have at least one input device (e.g., a keyboard, a mouse, a touchscreen, and the like) and at least one output device (e.g., a display screen, a printer, a wireless radio, and the like) depending on the nature of the device.

It should also be noted that there may be some elements that are used to implement at least part of the embodiments described herein that may be implemented via software that is written in a high-level procedural language such as object-oriented programming. The program code may be written in C, C++, Java, SQL or any other suitable programming language and may comprise modules or classes, as is known to those skilled in object-oriented programming. Alternatively, or in addition thereto, some of these elements implemented via software may be written in assembly language, machine language, or firmware as needed.

At least some of these software programs may be stored on a storage media (e.g., a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processors. The program code may be preinstalled and embedded during manufacture and/or may be later installed as an update for an already deployed computing system. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Various embodiments are described herein that generally relate to the assessment, optimization and improved control of an AD plant that uses an anaerobic digestion technique for processing organic waste materials. This can be done without having to add any additional materials such as enzymes, bacteria, nutrients or any other specific substances, for example. This can also be done without having to provide the existing AD plant by adding any additional operational processes such as phase separation, and pre/post treatment, for example. Rather, in accordance with the teachings herein, to optimize the AD plant's operation, certain values for input materials and operational settings, which are used by the AD plant, are selected over the time period of operation for the AD plant.

Accordingly, in one aspect, at least one embodiment described in accordance with the teachings herein can be used to increase the efficiency and optionally the financials of an anaerobic digestion facility without any new physical investment.

In another aspect, at least one embodiment described in accordance with the teachings herein can be used to determine values for optimal input and control variables that can be used in addition to incorporating additional processes and/or materials to improve the operation of the AD plant.

In another aspect, at least one embodiment described in accordance with the teachings herein can be used for the assessment of a given anaerobic operating facility (hereafter referred to as an "anaerobic digestion plant" or an "AD plant") before and/or after the construction of the anaerobic digestion plant. The methodology employed by such embodiments can also be referred to herein as an "off-line simulation" method. For existing AD plants, the off-line simulation method may then be used for retrofitting the AD plant so that its performance can be improved. At this first stage, a user may enter input data to define the AD plant that is to be simulated and other data for performing the simulation, visualizing the simulation results and generating reports.

In another aspect, at least one embodiment described in accordance with the teachings herein includes an optimization method that can be used in a second stage to optimize the operation of an AD plant after it has been assessed. This optimization methodology can also be referred to herein as a "near-line simulation" method. At this second stage, various possible scenarios can be simulated/generated and the best option according to some optimization criteria may be chosen to control the operation of the AD plant. The best option includes having at least one of: (1) certain values for input material variables, which can also be referred to as a "recipe", and (2) certain values for operational variables for various AD plant processes. For example, in at least one embodiment in accordance with the teachings herein multiple recipes may be used sequentially during the operation of the AD plant. For example, if the AD plant is operated for four months and the feedstock changes every month then there may be four recipes that are determined where each recipe is used for a unique one month period of the four month operation of the AD plant.

In another aspect, at least one embodiment described in accordance with the teachings herein may use a genetic algorithm for optimization.

In another aspect, in at least one embodiment described in accordance with the teachings herein, correlation measurements may be used to provide a set of recommended variables that are considered for optimization, as will be described in further detail below. The recommended variables are those that are estimated to have the greatest effect on the outputs that the user desires to maximize or minimize.

Figure 5:
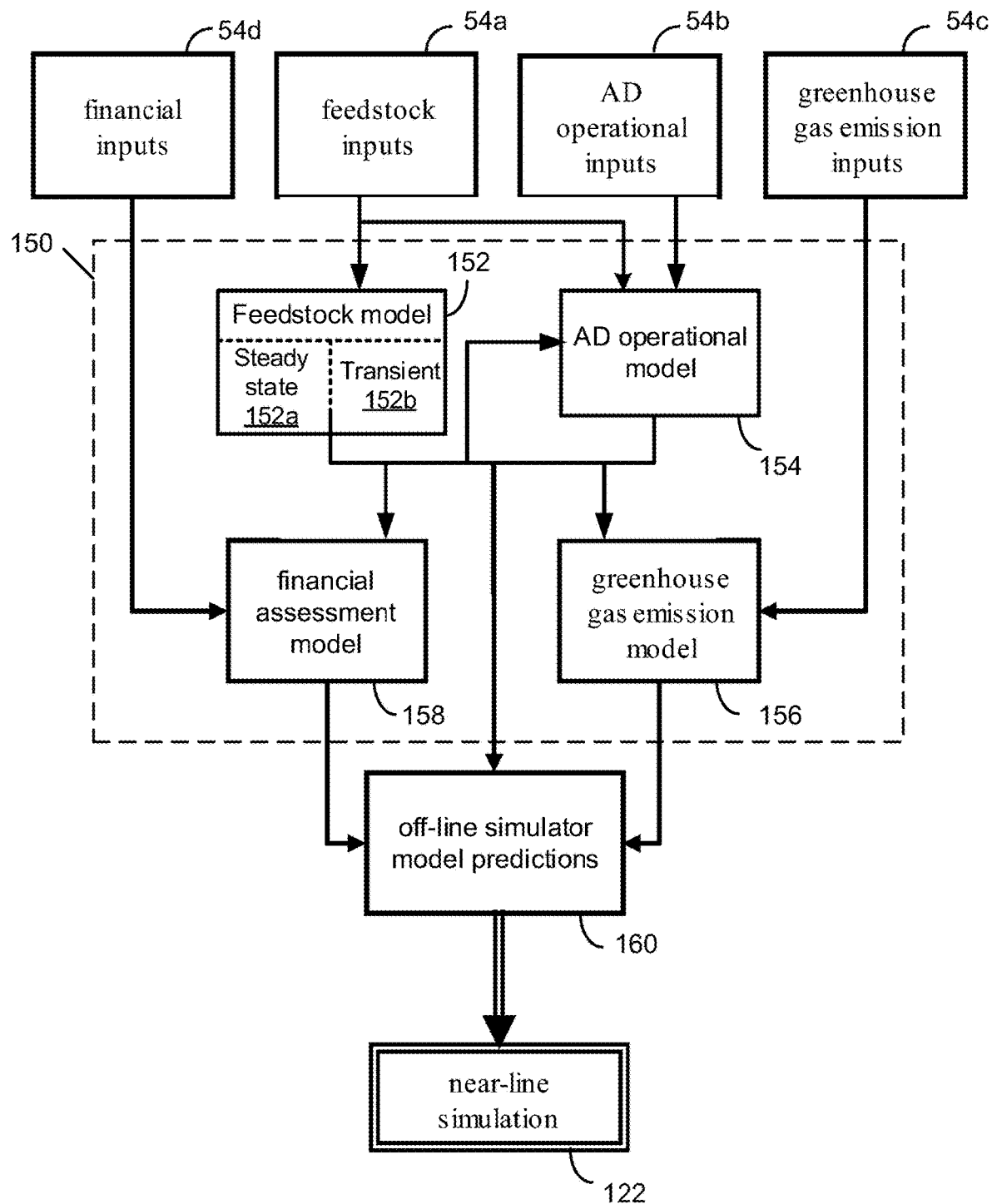
FIG. 5 is a schematic diagram showing the interaction between the various models that are used by the simulation engine to assess the operation of an AD plant in an example embodiment in accordance with the teachings herein.

In general, the assessment and optimization of an AD plant involves the assessment and optimization of the AD plant with respect to changes and fluctuations of the main feedstock flows, as well as operating conditions in order to efficiently operate the AD plant. The assessment is customizable and comprehensive compared to conventional methodologies for the assessment and optimization of an AD plant. For example, in at least one embodiment described in accordance with the teachings herein various models are used to more accurately define and assess the anaerobic digestion process and other aspects of the AD plant that runs the process. For example, these models can be used to simulate many or all aspects of the AD plant such as at least one of a technical, financial and environmental by using a greenhouse gas emission model, an anaerobic digestion financial model, a sensitivity and optimization model, and other models, which are described in greater detail. In at least one embodiment, an optimization model can be used without a sensitivity based on the input variables that are provided to the model and the function that is used by the model. An example embodiment of these models is shown in FIG. 5.

In another aspect, in accordance with the teachings herein, at least one embodiment includes a method that incorporates the use of artificial intelligence (e.g. machine learning) to improve the modelling and/or simulation of the AD plant. For example, the machine learning can be used to routinely validate and improve the models that are used by the off-line simulator. This machine-learning methodology can be referred to as an "online simulation" method that may be performed at a third stage.

In this third stage, the selected values for the input material variables and the operational variables are applied to the AD plant and the outputs are measured and compared to the anticipated outputs that are predicted by the machine learning model. If there is a discrepancy between the actual AD plant output and the predicted outputs, the machine learning parameters and the errors results are used to provide feedback to the off-line simulator to improve the models used by the off-line simulator. For example, high discrepancy values are included in the training order to teach the machine learning model how to handle corner cases (i.e. outliers). The inputs and outputs for real plant operation can also be used in the machine learning training data.

In another aspect, in accordance with the teachings herein, in at least one embodiment the above methods can be implemented in a three-stage process for improving the anaerobic digestion facility operation and optimal process control. The three stage process can be used to design new anaerobic digestion biogas plants and to optimize the operation of existing anaerobic digestion biogas plants. The three-stage process includes the off-line simulation method, the near-line simulation method and the online simulation method performed by the off-line, the near-line and the online simulators. This combination of off-line, near-line and on-line simulators has not been used before and provides a robust, intelligent, comprehensive, and customizable approach for anaerobic digestion process simulation as well as optimal AD plant control.

For example, the three-stage process begins with the off-line simulation method, and then moves to the near-line simulation method that uses the analytical results of the off-line simulation method to optimize values for the input material variables and/or the AD plant operating variables. These two parts of this three-stage process (i.e. the off-line and near-line simulation methods) can be used for pre-design of anaerobic digestion plants as well as in retrofitting and assessment of existing anaerobic digestion plants. This makes the developed approach quite general as it can be used for the project pre-design as well as the operation of existing anaerobic digestion plants.

The three-stage process then moves to the on-line simulation method which uses the optimized values for the variables from the near-line simulation method and uses machine learning to develop a machine learning model (i.e. neural-network model) that is used to predict the operation of the AD plant. The predicted operational results of the neural network model can then be compared to the actual real-time data obtained from a given AD plant to tune the neural network model and improve its performance. The changes made to the neural network model can then be fed back to the off-line analytical models to improve the anaerobic digestion simulator. After the initial simulation using the machine learning method, further simulations with the neural network model leads to further tuning of the model for further improved performance which may lead to further tuning of the analytical models used by the near-line simulator to improve the operational results depending on the operational goals (i.e. maximization of certain variables and/or minimization of other variables). This tuning of the analytical models may include adjusting the coefficients that are used in these models as well as adding additional numerical terms. Accordingly, the on-line simulation method may also be referred to as a tuning method for tuning and improving the operation of the simulator to achieve certain optimization goals.

Referring now to FIG. 1, shown therein is a block diagram of an example embodiment of a system 10 for performing at least one of assessing an AD plant, optimizing an AD plant, tuning a simulator for simulating the AD plant and optionally controlling the operation of an AD plant where in each case the AD plant employs an anaerobic digestion process. The system 10 comprises a server 12, a simulation engine 14, a database 16 and a user interface 18. The simulation engine 14 comprises an administrator 20, a computation scheduler 22 and computation nodes 24 for performing various types of simulations for one or more users. A user can use a user browser 28 to interact with the user interface 18 via a network 26.

It should be noted that the embodiment of the system 10 is an example and there can be other configurations for the system 10. For example, in an alternative embodiment, the system 10 generates input material settings and operational settings, as one or more recipes that can then be provided to a plant controller 30 that controls the operation of an AD plant. In such embodiments, the network 26 may be a local network that the user may use to interact with the user interface 18.

In other alternative embodiments, the system 10 may be directly interfaced with the plant controller 30 and the AD plant (not shown) such that the system 10 receives real-time data about the operation of the AD plant. This real-time data may be obtained from various sensors that are used at the AD plant. Sensors may include but are not limited to, biogas production sensors, mass flow rate sensors, electricity generation sensors, feedstock and digestate characteristic sensors. The system 10 then performs simulations to achieve or maintain certain optimal target operating conditions, which may include generating updated input material settings and/or operational process settings to achieve the optimal target operating conditions. The system 10 then sends the input material settings and/or the operational process settings, which may be updated, to the plant controller 30 which then controls the operation of the AD plant to achieve the optimal target operating conditions. The measurements from the AD plant and simulations to generate the settings can be done periodically such as, but not limited to, every 0.5, 1, 4, 8, 16 or 24 hours, for example, in order to maintain the optimal target operating conditions.

The server 12 includes at least one computing device that is used to perform the simulation and to control processes described herein. Accordingly, the server 12 executes the simulation engine 14 for performing at least one of assessment, optimization, monitoring and control of an AD plant. The server 12 also generates the user interface 18 for receiving input data and commands from a user. The server 12 may also use the user interface 18 for performing at least one of providing simulation and/or optimization results to the user, allowing the user to monitor and/or control variables, and provide corresponding reports on one or more of the aforementioned items to the user.

The server 12 may be implemented using one computing device that has one or more processors, a communication interface such as one or more network adaptors or communication modules such as a high speed modem, Input/Output (I/O) hardware, a power module for providing power to the server components and a memory unit. The memory unit comprises software code for implementing an operating system, various programs, and the simulation engine 14. Alternatively, the server 12 may comprise more than one of these computing devices depending on the computational load. These computing devices can be implemented using a desktop computer, a laptop, a mobile device, a tablet, and the like if they provide adequate processing power such that simulations can be done in a reasonable time frame. For example, in some cases the simulations may have to be done in real-time when the server 12 is directly coupled with, and sending control instructions to, a plant controller 30. In some embodiments, such as the example embodiment of FIG. 1, the server 12 can be a webserver that users can access via the Internet.

In some embodiments, the server 12 can be dynamic in hardware architecture. For example, the server 12 may be implemented using just one computing device and the number of concurrent computations that can be provided by the simulation engine 14 is limited to the number of threads that the computing device is able to run in parallel. These computations are handled by the administrator 20 and the computation scheduler 22 and are placed in a queue for processing by one or more computation nodes 24. However, as further computations are needed due to the amount of simulations, optimization and/or tuning (i.e. machine learning) being performed by one or more users, the queue is likely to be filled and more resources are then needed for performing computations.

For example, a given simulation task is divided into a number of small computations which are delegated to the computation nodes 24. The queue size which is comprised of the computations to be performed in the future and the average waiting time of each task may both be used as metrics to assess the currently available computational power. These metrics can be modified by combining the average waiting and computation time of a whole simulation process (e.g. adding the waiting times of all computations for a single simulation or optimization process). For example, such metrics can be evaluated specifying a maximum wait time of 2 minutes, 10 minutes, one hour etc. Should the specified metric lie above the predefined threshold, a resizing of the system can be initiated to perform the computations more quickly. At that point, the resizing may involve expanding the server 12 to include more machines to provide more processing cores that can be used to perform more concurrent computations. The computation speed and number of concurrent threads benefit when using more powerful computing devices.

The simulation engine 14 receives requests for performing certain operations such as simulations, optimizations, and tuning of certain models used by the simulation engine 14. The simulation engine 14 relays these requests to the administrator 20, which then works with the computation scheduler 22 to obtain the results related to the requests. Once the results are computed, the server 12 obtains the results from the simulation engine 14 and then allows the user to access the results and/or generate reports based on the results via the user interface 18. In at least one embodiment, the simulation engine 14 may be implemented in a Java Virtual Machine (JVM) using the Java programming language.

In embodiments in which the system 10 is communicatively coupled to the plant controller 30, the server 12 can obtain values for control variables from the simulation engine 14 based on the optimization that has been done. The server 12 can then send the control values to the plant controller 30 for implementation. The plant controller 30 can also send measurements on certain input materials such as, but not limited to, remaining quantity of one or more feedstocks, for example, and operating variables to the server 12 which can then instruct the simulation engine 12 to perform monitoring and updating/tuning of the models that are used to obtain more accurate control values for achieving certain optimization criteria.

The database 16 is used to store the values for input variables that are provided by the user as well as other data that is used for simulation, optimization, monitoring and/or tuning. The database 16 can also store inputs from the user as well as simulation and optimization results for generating reports for a particular simulation or optimization. The database 16 can be stored in the memory of the server 12. Alternatively, the database 16 can be stored in one or more separate data stores provided by secondary storage devices, such as solid state drives, for example. Accordingly, the database 16 can be distributed over several database nodes on different devices which allows for database scaling.

In order to deal with the amount of data that is used and generated in the simulations, the structure of the database 16 is implemented such that data structures are divided into data packages. This allows all data objects to be structured hierarchically rather than saving all important fields for an object in one layer. A simulation package for example can be structured into an input package, an output package and intermediate computational results. These packages can be organized further. The input package can for example be divided into feedstock inputs, financial inputs, process inputs, simulation criteria, etc. This way, when a user requests to review or change a specific field, only this specific package has to be retrieved to show existing parameters and only this specific package has to be sent back to the server 12 for an update in the database 16 if changes were made. The procedure reduces computation time at the server 12 and results in a shorter response time when performing simulation, optimization, monitoring and/or model updates.

In some embodiments, when more than one computing device is used to implement the server 12 to improve efficiency and deal with large data sets that are to be computed, the database 16 can be stored on multiple computing devices, which can be considered as different database nodes for a distributed database. In this case, common data sets can be duplicated across different database nodes so that frequently accessed data is available in multiple places and users do not have to wait for each other when accessing the common data sets. Therefore, the amount of communication between the computation nodes 24 is reduced and is spread across multiple network channels.

The administrator 20 is a software program that receives user requests from the server 12 and manages the completion of the requests. Depending on the requests, the administrator 20 either performs the request, such as for short (i.e. computationally easy) tasks, or informs the computation scheduler 22 that a computation is to be performed, such as in the case of computationally heavy tasks. Examples of short tasks include, but are not limited to, data storage, data retrieval, account creation, and the login process. Examples of long tasks include, but are not limited to, certain computations such as simulations, sensitivity analysis, and optimization requests. A task ID is assigned to each computation request as well as a request type and the variable values for each request are stored in the database 16.

The computation scheduler 22 is a program that can be used to create a number of tasks (i.e. software threads) which can be instances of the Java™ java.lang.Runnable class for performing different functions in parallel. In alternative embodiments, other programming languages that are capable of multi-threading can be used. Each request is separated into tasks that can be run in parallel. The division of the request depends on its complexity and type. A number of task slots, depending on the currently present computational structure, can be defined for performing tasks in parallel. If a task slot is free, an incoming task is assigned to the free task slot and started. It can be referred to as a running task. If all of the task slots are occupied, the computation scheduler 22 creates a queue for the tasks that are waiting to be assigned to a task slot. The computation scheduler 22 then picks a waiting task once a running task is finished. Scheduling can be performed on a First Come-First Serve (i.e. FCFS) basis, a shortest job first basis or a longest job first basis. Tasks may be scheduled for multiple scenarios, multiple AD plants and a number of different clients (i.e. different users).

In some embodiments, the computation scheduler 22 can also reorder the priority of clients that are making task requests when determining the order in which tasks are performed. For example, the priority of a user that is making a request requiring a high number of computations can be lowered in order to compute the requests of other users that require a lower number of computations. In this case, the assumption is that a request with a low number of computations means a more urgent request, which also allows the computation resources to be freed faster for such tasks.

The computation nodes 24 represent the task slots that are available for performing tasks. When one of the computation nodes 24 is free, a task that is waiting in the queue is provided to the free computation node 24. The free computation node 24 receives a task ID and a computation type (e.g. simulation, sensitivity analysis, optimization, machine learning model, report generation, or visual result preparation) and is considered to be an active computation node. The active computation node then retrieves the variables from the database 16 that are associated with the task by using the unique task ID and then performs the computation. Once the computation is completed, the results are stored in the database 16 and the computation scheduler 22 is notified that the active computation node is now a free computation node. The number of computation nodes 24 depends on the number of machines that are used to implement the server 12 as well as the number of possible parallel threads for each of the machines.

The user interface 18 is generated by the server 12 and provides a number of graphical user interfaces (GUIs) that the user can interact with to perform various actions. For example, the user can enter one or more of the following:
(a) project input values to define a new simulation project or access a previously created simulation project and perform further simulations, optimization, tuning and/or analysis;
(b) input values to define an AD plant that is to be simulated;
(c) simulation control values to define how the simulation is to be performed; and
(d) report control values to define how the results of the simulation are to be reported.

The user can interact with the user interface 18 over the network 26 depending on the implementation of the system 10. For example, when the server 12 is a webserver, the network 26 is the Internet and the user can access the user interface 18 using an Internet browser as the user browser 28. In other embodiments, the server 12 can be a private server, the network 26 is a local area network and the user can access the user interface 18 using a local program as the user browser 28.

Figure 2:
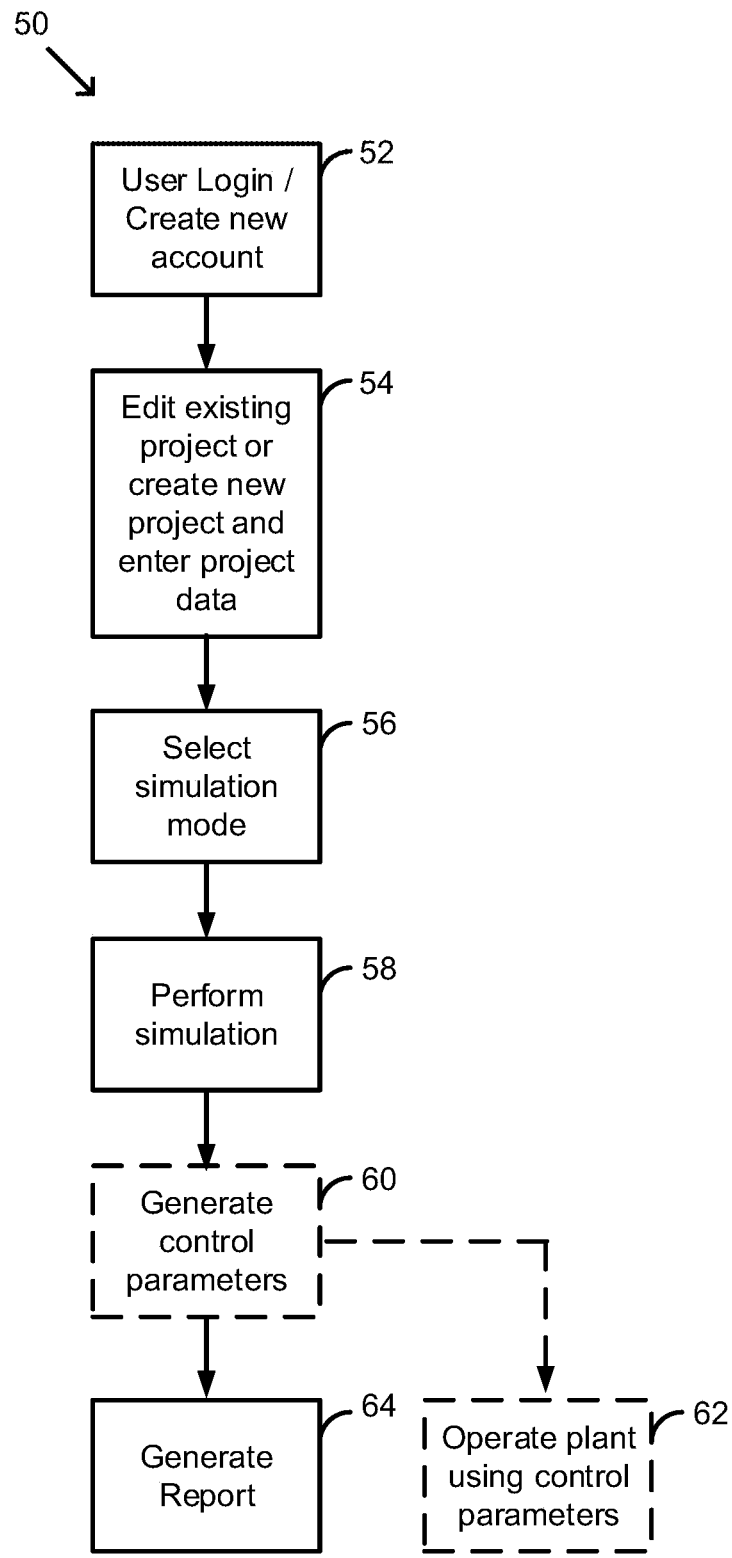
FIG. 2 is a flowchart of an example embodiment of a method for performing at least one of assessing, optimizing, monitoring and optionally controlling the operation of an AD plant as well as viewing the results.

Referring now to FIG. 2, shown therein is a flowchart of an example embodiment of a method 50 for performing various operations including at least one of assessing, optimizing, monitoring/tuning and optionally controlling the operation of an AD plant that employs an anaerobic digestion process as well as viewing the results of the operation. The method 50 can be performed by the system 10.

The method 50 begins at act 52 where a user logs in at the user interface 18 to access the server 12. The server 12 can check the database 16 to verify the account and login credentials of the user. If the user does not already have an account then the user can create a user account at act 52.

At act 54, the user can open an already existing project where data about the AD plant has already be entered. Alternatively, at act 54, the user can define a new project for performing a simulation of an AD plant. The user can enter various project data about the new project including at least one of a project name, dates of operation, feedstock availability and quantity, location of the AD plant, operational objectives, members of the project, values for various variables for defining the AD plant and various data for performing simulations, optimization and/or creating reports.

Figure 3:
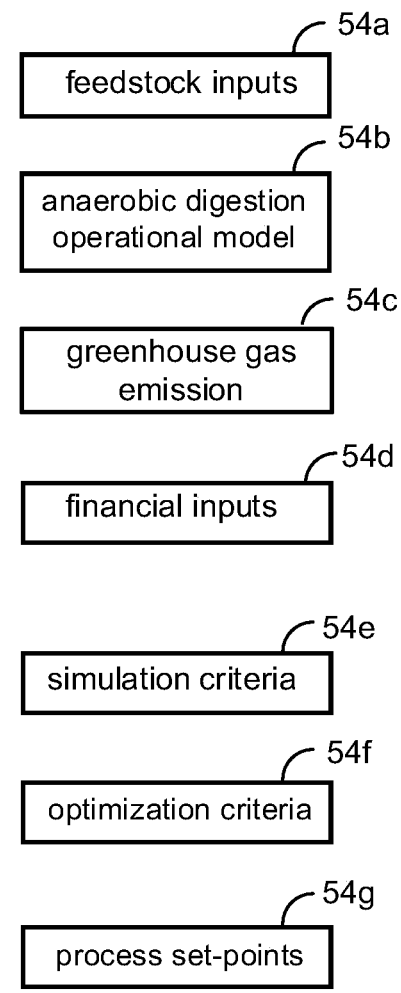
FIG. 3 illustrates various input, simulation and report variables that can be specified by the user for defining an AD plant, performing simulation and generating reports.

Examples of various input, simulation and optimization variables 54*p* that can be specified by the user for defining an AD plant, performing simulation and generating reports are shown in FIG. 3. The input variables include feedstock inputs 54*a*, anaerobic digestion operational inputs 54*b*, greenhouse gas emission inputs 54*c*, and financial inputs 54*d*. The simulation variables include simulation criteria 54*e* and the optimization variables include optimization criteria 54*f*, process set points 54*g* and sensitivity analysis inputs (not shown).

The feedstock inputs 54*a* include data on the quality, quantity and availability of the feedstocks that are used. These feedstocks may further be categorized as at least one of municipal, energy crops, and agriculture, for example. For municipal inputs, examples include, but are not limited to, biosolids such as primary or secondary sludge and organics such as sort separated organic material.

For agriculture, the user can specify one or more of a type, a quality, a quantity, availability (e.g. mass and period), physical-biochemical properties, proximate-ultimate analysis, organic fraction composition, and energy contents. Examples of agriculture type include, but are not limited to, alfalfa and manure and other agricultural sources that can be used in the AD process. Examples of quality include, but are not limited to: alfalfa, hay, grass, cow, poultry, and sheep for manure. Examples of quantity include but are not limited to, one or more of mass, density, and period of time over which it is available. Examples of physical-biochemical variables include, but are not limited to, one or more of volatile solids, biochemical oxygen demand, chemical oxygen demand and total solids, biodegradability VS, biodegradability COD, pH, phosphorous, sodium content, and potassium content). Examples of proximate-ultimate include, but are not limited to, one or more of carbon, hydrogen, nitrogen, sulphur, oxygen, ash content, volatile matter and fixed carbon. Examples of organic fraction for the agriculture type include, but are not limited to, one or more of lipids, carbohydrates, protein and fiber. Examples of energy content include, but are not limited to, one or more of biochemical methane potential, higher heating value and lower heating value.

The anaerobic digestion operational model inputs 54b include variables for specifying the bioconversion for the AD plant. The bioconversion variables can include one or more of process characteristics, system characteristics and expected products. Examples of process characteristics variables include, but are not limited to, one or more of process temperature, targeted total solid and hydraulic retention time. Examples of system characteristics variables include, but are not limited to, one or more of overhead volume, electrical and thermal efficiencies, use AD plant nominal capacity (i.e. yes or no), generated products (e.g. electricity, thermal, biomethane, biogas and biofertilizer) and consumed fuels (e.g. diesel fuel, ethanol (100%), liquefied natural gas, liquefied petroleum gases and motor gasoline). The consumed fuels can be specified on a quantity per usage increase. For the expected products, the user can specify the type and/or the characteristics of these products.

The greenhouse gas emission inputs 54c include various variables such as, but not limited to, one or more of the product generated, fuel/energy sources consumed, emission factors, pricing (such as carbon credit price), current waste disposal situation and transportation infrastructure. The product generated variables can include, but are not limited to, one or more of electricity, natural gas, biomethane and biofertilizer. Emission factors for electricity can be specified based on custom data or data from the database 16. The fuel/energy sources consumed variables include, but are not limited to, diesel fuel, natural gas, biodiesel, and coal. The current waste disposal situation variable can be specified as being one or more of a certain percentage of landfill (burn), a certain percentage of incineration (e.g. agricultural, energy crops, biological materials, forest materials and municipal materials), and a certain percentage of composting (municipal materials and all other materials) where these three percentages add to 100%. The emission factors can be obtained from the database 16 based on the type of feedstock, products, or fuels; the location of the plant and the regulations in the area also play a role in the selection of the dataset; alternatively, all those emission factors may be provided by user input. The emission factors may also include a geographic location or region of the AD plant that the user can choose from and emission pricing factors for the selected region will apply. For example, the regions can include, but are not limited to, AKGD (ASCC Alaska Gold), AKMS (ASCC Miscellaneous), CAMX (WECC California), ERCT (ERCOT All) and FRCC (FRCC All). The carbon credit price can be set based on user input (such as price per CPI) or data from the database 16 which includes carbon taxes for various locations such as, but not limited to, California CaT, Chile carbon tax, Chongqing pilot ETS, Columbia carbon tax and Denmark carbon tax.

The financial inputs 54d include various variables including, but not limited to, pricing and/or costs for one or more of feedstock financials, bioconversion, operation costs, insurance costs, maintenance costs, labor costs, plant capital investment, land costs, generated product such as electricity, heat, digestate; consumed fuel/energy source such as diesel, biodiesel, and coal; investment model and plant capital investment variables. The feedstock financials include data on one or more of pricing, transportation costs and transmission costs. The plant capital investment can be specified as investment in total (e.g. capex) or investment per module (e.g. pre/post processing capital investments), The investment model can be further specified in terms of loan type, reserved fund and related inputs.

The simulation criteria inputs 54e include one or more of recommended input variables, user selected input variables, user selected output variables, steady-state simulation variables and transient simulation variables. The recommend input variables can be specified by the simulation engine 12. For example, a correlation measure, such as the Pearson correlation coefficient or the Spearman correlation coefficient, can be used to provide the recommended inputs. This technique includes generating a number of randomly generated sets of values for the input variables, performing simulations on those randomly generated sets based on the desired maximization/minimization goal, and then analyzing the results to determine which input variables influence the end result the most by determining which input variables are more closely correlated with the desired outputs. Those input variables that are most correlated are then included in the set of recommended parameters (i.e. recommended input variables) in an ordered manner with those variables having the highest correlation being listed first.

Examples of user selected input variables include various variables such as, but not limited to, one or more of agriculture such as alfalfa, or hay price; municipal variables such as biosolids primary sludge price, or organic source separated price, generated electricity price, generated biofertilizer price, capex capital cost, capex installation cost, or an insurance price.

Examples of user selected output parameters include, but are not limited to, one or more of labor costs, maintenance costs, major maintenance costs, future fund costs, loan costs, power generated income, GHG carbon credits saved, feedstock costs, feedstock tipping fees, annual income, annual cost, cumulative cash flow, annual cash flow, cash flow available for debt, Internal Rate of Return (IRR), Net Present Value (NPV), Payback Period (PBP), and Principal Income (PI).

The simulation criteria also includes specifying initial conditions and steps for steady-state simulation and/or transient simulation variables. The transient simulation will consider the effect of hydraulic retention time (HRT) on the results and in the steady state simulation the HRT is a constant value. For steps, the user can also specify the minimum value and maximum value and the number of iterations (to determine a step-size) to perform the optimization. For example, if the minimum value is 0, the maximum value is 50 and the number of intervals are 100, then the step-size is 0.5. Alternatively, the user can specify the percentage by which the input variables that are used for optimization can change and specify the number of iterations for the maximum and minimum values that result from this percentage change from which the step-size can be determined. For example, if the user sets the percentage to +/−20% and the number of intervals to 100, then if the value of a selected input variable based on the off-line simulation is 10, then for sensitivity analysis the minimum value is 8 and the maximum is 12 and the step-size is (12−8)/100=0.04.

The optimization criteria inputs 54f can include various goals such as maximizing a particular variable and/or minimizing a particular variable. Some examples include maximizing methane production, minimizing the leftover feedstock, and/or maximizing the financials. Alternatively, an optimization criteria can include a combination of maximizing two or more parameters, minimizing two or more parameters, minimizing at least one parameter, maximizing at least one parameter or keeping a parameter in a predefined range. For example, the goal may be a function that is a weighted combination of two or more products such as maximizing a function f(biogas, greenhouse gas)=0.4*(biogas)+0.6*(greenhouse gas), or maximizing a function f1(biogas, feedstock leftover)=0.5 * biogas−0.5 * feedstock leftover, for example. In the second example, the maximizing of biogas production and the minimizing of feedstock leftovers are combined as an optimziation goal. The minimization optimization of feedstock is inverted by a coefficient in function f1, which allows one to treat the whole goal as a maximization.

The process set points inputs 54g include various operational variables that the user can set in order to achieve results within an expected range such as, but not limited to, one or more of achieving a certain targeted amount of total solids in the mixture, achieving a certain carbon/nitrogen ratio (C/N ratio), and achieving a certain organic loading rate (OLR), for example.

Referring once again to FIG. 2, at act 56, the user can select a simulation mode to perform. This can include performing an off-line simulation, a near-line simulation, an on-line simulation or certain combinations thereof. For example, an—off line simulation followed by a near-line simulation can be performed. Alternatively, an off-line simulation, a near-line simulation and an online simulation can be performed.

At act 58, the selected simulation is performed. An example embodiment of a method for performing an off-line simulation is described in more detail with respect to FIGS. 4 and 5. An example embodiment of a method for performing a near-line simulation is described in more detail with respect to FIGS. 6 and 7. An example embodiment of a method for performing an online simulation is described in more detail with respect to FIGS. 8 and 9.

At act 60, if the method 50 performed a simulation which includes optimization (i.e. the near-line simulation), then the method 50 can generate values for certain control variables that can be used to optimize the performance of the AD plant. The optimal values for the control variables may then be used to control the AD plant at act 62. For example, this control may be done automatically for embodiments in which the server 12 is directly connected to the plant controller 30.

At act 64, the method 50 generates a report based on various parameters that can be specified by the user. Act 64 may be optional in some cases and not be performed. For example, the user can perform one or more of the following:

(a) specify result presentation settings such as graph, table; results/analysis and currency;
(b) set alternative sensitivity scenarios such as, but not limited to, one or more of maximum electricity price, minimum electricity price, maximum sludge tip fee and minimum sludge tip fee;
(c) define generating a new report for the simulation(s) to be done or adding the simulation results to an existing report; and
(d) add various sections to the report, which may include showing the results of certain aspects of the simulation in a table or graphical form and entering text to further describe the simulation that is being done.

Figure 4:
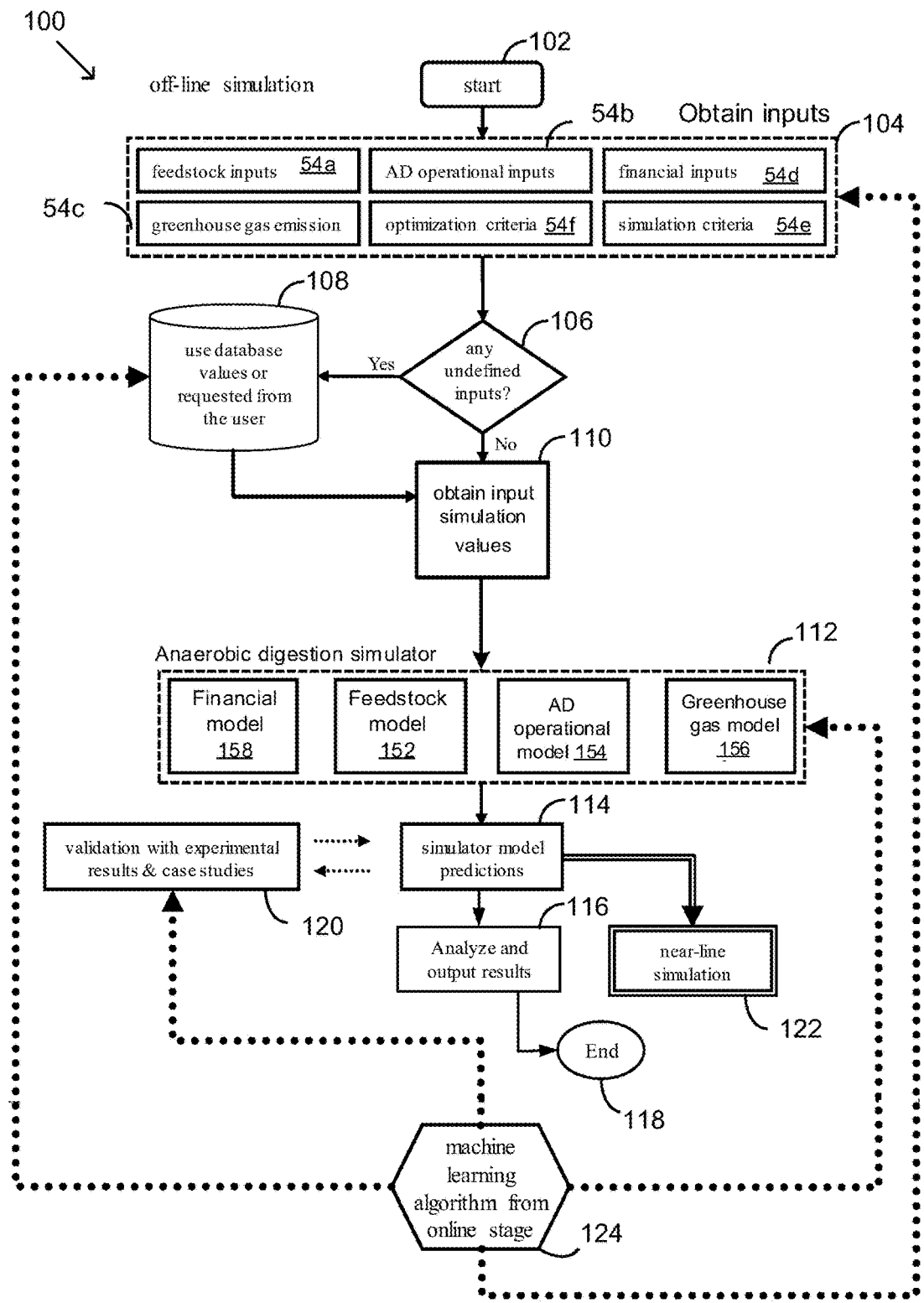
FIG. 4 is a flowchart of an example embodiment of a method of performing an off-line assessment of an AD plant that employs an anaerobic digestion process.

Referring now to FIG. 4, shown therein is a flowchart of an example embodiment of a method 100 for performing an off-line assessment of an AD plant that employs an anaerobic digestion process. The method 100 begins at act 102 when the user has chosen to perform an off-line simulation.

At act 104, the method 100 obtains values for various input variables that may be used for near-line simulation. At this act, the input variables include, but are not limited to, data for one or more of the input feedstock variables 54a, the anaerobic digestion operational process variables 54b, the financial input variables 54d, the greenhouse gas variables 54c related to the specific project, along with the corresponding set-points, the optimization criteria variables 54f and the simulation criteria variables 54e. The values for these input variables are used to define the project and the operational model. The user may initially provide these values to define the operation of an AD plant that they wish to simulate. The user may enter these input variable values once and after that the simulation engine 14 will update the values as needed, as will be described in further detail herein.

At act 106, the method 100 determines whether there are any input variables that have not been provided with values by the user. If this is not the case then the method 100 proceeds to act 110. If this is the case then the method 100 proceeds to act 108 where the database 16 is used to obtain the missing values for the variables. For example, the database 16 may be used to provide values for feedstock characteristics. However, unknown parameters and financials inputs regarding the feedstocks will generally be requested from the user. Also if the database 16 does not specify a value for a particular variable that is missing then the user can be queried to provide this value. The method 100 then proceeds to act 110.

At act 110, the method 100 obtains input simulation values that are to be used by the anaerobic digestion simulator at act 112. This is based on the analytical models that are used by the anaerobic digestion simulator 112 and the values that are used by these models.

At act 112, the method 100 performs a simulation for the project using developed analytical models to generate the near-line simulation predictions, which are then saved in the database at act 114, as part of the off-line simulation. An example of the developed analytical models is shown in FIG. 5.

Referring now to FIG. 5, shown therein is a schematic diagram of the models and data that are used by an example embodiment of the anaerobic digestion simulator 150 as well as the interaction between the various models. The simulation engine 14 runs the anaerobic digestion simulator model 150 to assess the operation of an AD plant that was specified by the user. The simulator model 150 includes a feedstock model 152, an Anaerobic Digestion (AD) operational model 154, a greenhouse gas emission model 156 and a financial model 158. The feedstock model 152 may be a steady state feedstock model 152a that is used for steady state simulations or a transient feedstock model 152b that is used for transient simulations. The user can select whether to use the steady state feedstock model 152a or the transient feedstock model 152b. Alternatively, the use of the steady state feedstock model 152a or the transient feedstock model 152b may be dictated by the type of data that is available from the AD plant. The steady state feedstock model 152a generates the biochemical methane potential (BMP) for a given time interval that is simulated while the transient feedstock model 152b can generate a curve for the BMP during the given time interval that is simulated. It should be noted that the financial model 158 and the greenhouse gas emission model 156 are optional in cases where simulations are performed without any financial parameters.

The results from running a simulation of the feedstock model 152, the AD operational model 154, greenhouse gas emission model 156 and the financial model 158 are combined to provide the off-line simulator model predictions 160. If the user also wishes to optimize the input material settings and the AD plant's operational values, then this results in the determination of off-line simulator model predictions 160 at 114 of method 100. These predictions can then be provided to the near-line simulator, an example implementation of which is provided by method 200.

The steady state feedstock model 152a utilizes the feedstock inputs 54a along with three different sub-models in feedstock analysis to determine the BMP, which is fundamental to the AD plant's operation and is the starting point of the feedstock model 152. For example, the three sub-models can be theoretically derived based on: (1) chemical oxygen demand (COD) (see equations 1a and 1b (Lesteur et al., 2010)), (2) elemental composition analysis (e.g. C, H, N, S, O) (see equations 2a and 2b (Raposo et al., 2011)) and (3) the organic fraction composition (OFC) (see equation 3 (Tarvin et al., 1934)) to calculate the BMP values. The theoretical equations for these sub-models are as follows:

$$BMP_{COD} = \frac{\eta_{CH_4} RT}{pVS_{added}} \tag{1a}$$

$$\eta_{CH_4} = \frac{COD}{64(gr/mol)} \tag{1b}$$

where:
$\eta_{CH_4}$ is the molar concentration of methane ($CH_4$);
R is a constant for the gas used in the AD plant;
T is temperature in the digester;
p is the pressure in the digester;
$VS_{added}$ is Volatile Solids added;
COD is the chemical oxygen demand of the digester which can be measured; and
$BMP_{COD}$ is the biochemical methane potential due to the chemical oxygen demand of the digester.

$$C_n H_a O_b N_c + \left(n - \frac{a}{4} - \frac{b}{2} + \frac{3c}{4}\right) H_2 O \rightarrow \tag{2a}$$

$$\left(\frac{n}{2} + \frac{a}{8} - \frac{b}{4} - \frac{3c}{8}\right) CH_4 + \left(\frac{n}{2} - \frac{a}{8} + \frac{b}{4} + \frac{3c}{8}\right) CO_2 + cNH_3$$

$$BMP_{EC} = 22.4(n/2 - a/8 - b/4 - 3c/8) / (12n + a + 16b + 14c) \tag{2b}$$

where:
a, b, c, n are variables to be solved;
equation 2a represents the elemental composition of the feedstock and equation 2a can change depending on changes in the makeup of the feedstock;
EC is elemental composition; and
$BMP_{EC}$ is the biochemical methane potential due to the elemental composition.

$$BMP_{OFC} = 415 \times \% \text{ carbohydrates} + 496 \times \% \text{ proteins} + 1014 \times \% \text{ lipids} \tag{3}$$

where:
% carbohydrates is the proportion of the feedstock that is made up of carbohydrates;
% proteins is the proportion of the feedstock that is made up of proteins;
% lipids is the proportion of the feedstock that is made up of lipids; and
$BMP_{OFC}$ is the biochemical methane potential due to the organic fraction composition.

The transient feedstock model 152b utilizes the feedstock inputs 54a along with at least one of a number of different sub-models in feedstock analysis to determine the transient biochemical methane potential (BMP). The parameter M(t) represents the cumulative methane yield which corresponds to the BMP but is in transient form. The theoretical equations for some transient feedstock sub-models that maybe used follow below. These sub-models may incorporate kinetic models that are applied to the anaerobic digestion process to simulate the transient trends of biogas production.

For example, the first order kinetic model may be used by the transient model 52b according to equation (4) and as described in Dennehy et al. (2016); Kafle and Chen (2016) and Xie et al. (2011).

$$M(t) = P * [1 - \exp(-kt)] \tag{4}$$

Alternatively, the Chen and Hashimoto model is another example of a transient sub-model that may be used by the transient model 52b according to equation (5) and as described in Me et al. (2013).

$$M(t) = P * \left[1 - \frac{K_{CH}}{HRT \times \mu_m + K_{CH} - 1}\right] \tag{5}$$

Alternatively, the Modified Gompertz model is another example of a transient sub-model that may be used by the transient model 52b according to equation (6) and as described in Xie et al. (2011) and Zhao et al. (2016).

$$M(t) = P * \exp\left\{-\exp\left[\frac{R_{max} \cdot e}{B_0}(\lambda - t) + 1\right]\right\} \tag{6}$$

Alternatively, the Dual pooled first order kinetic model is another example of a transient sub-model that may be used by the transient model 52b according to equation (7) and as described in Dennehy et al. (2016) and Rao et al. (2000).

$$M(t) = P * [1 - \alpha \cdot \exp(-K_f t) - (1-\alpha) * \exp(-K_L t)] \tag{7}$$

The various variables used in equations 4 to 7 are defined as follows.

M is the cumulative methane yield $$\left(\frac{mL}{grVS}\right);$$

P is the ultimate methane yield $$\left(\frac{mL}{grVS}\right);$$

t is the digestion time (day);
k is the first order rate constant $$\left(\frac{1}{day}\right);$$

$K_{CH}$ is Chen and Hashimoto kinetic constant (dimensionless);
HRT is the digestion time or hydraulic retention time (day);
$\mu_m$ is the maximum specific growth rate $$\left(\frac{1}{hour}\right);$$

$R_{max}$ is the maximum methane production rate $$\left(\frac{\frac{mL}{grVS}}{day}\right);$$

e is the constant 2.7183;
$\lambda$ is the lag phase (day);
B is the microorganism concentration $$\left(\frac{gr}{liter}\right);$$

$K_f$ is the rate constant for rapidly degradable substrate (1/day);
$K_L$ is the rate constant for slowly degradable substrate (1/day); and
$\alpha$ is the ratio of rapidly degradable substrate to total biodegradable substrate (dimensionless).

With regards to steady state simulations, the ability to determine each of the $BMP_{COD}$, $BMP_{EC}$, and $BMP_{OFC}$ depends on whether values needed for the variables used in equations 1a to 3 are available. If two or three of the BMP values are determined then the overall BMP of the AD plant may be the average of the determined BMP values. If only one BMP value is determined then this is set as the overall BMP of the AD plant. A user may select which of the BMP values to be simulated or whether at least two of the BMP values are to be simulated and combined. The output of the steady state feedstock model 152a is therefore an estimate of the overall BMP of the AD plant. It should be understood that the equations 1a to 3 are subject to change and in other embodiments other equations, as is known to those skilled in the art, may be used for steady state simulation.

With regards to transient simulations, the ability to determine the M(t) for each of equations 4 to 7 depends on whether the values needed for the variables used in equations 4 to 7 are available. If two, three or four of the M(t) values are determined then the overall M(t) of the AD plant may be the average of the determined M(t) values. If only one M(t) value is determined then this is set as the overall M(t) of the AD plant. A user may select one of the sub-models to be used or whether a combination of the sub-models to be used for simulation. The output of the transient feedstock model 152b is therefore an estimate of the overall M(t) of the AD plant. It should be understood that the equations 4 to 7 are subject to change and in other embodiments other equations, which are known to those skilled in the art, may be used for steady state simulation.

The AD operational model 154 receives the feedstock inputs 54a, the AD operational inputs received from the steady state feedstock model 52a or the transient feedstock model 52b, and the overall BMP of the AD plant so that it can use the overall BMP value or the M(T) value, the feedstock quantities, and the feedstock availabilities to determine the AD plant's bio-methane, electricity, and thermal production capacities. The feedstock availability means the supply of feedstock that is available for certain time intervals during the entire time period over which the simulation is done. For example, the supply of a feedstock can change every month so its availability will change depending on the month that is being simulated during the simulation of the overall time period. The AD operational model 154 can determine the estimated AD plant outputs such as bio-methane, electrical and thermal energy by:

1) using a digester equation which calculates the digester working volume which is the volume required in order to operate the digester based on the availability of feedstocks and the feedstock quantities (the digester equation is based on mass and volume flow rates and incorporates standard calculations known in this art; e.g. how much mass is input to the digester will determine how much water is added to reach the required Total Solids (TS) for the process); and 2) using a digestate equation and a biofertilizer equation to calculate the generated digestate and the generated bio-fertilizer during the anaerobic digestion process (these equations are based on mass and volume flow rates and are standard calculations known in this art).

These three equations are developed based on the volume of inflows and outflows in the digester and are based on mass balance equations. The volumes of the input materials are considered in order to meet the operational conditions of the facility. For example, the bio-methane potential, electricity and thermal outputs of the plants are calculated from the feedstock analysis models along with the BMP models. This may be done by determining, from either the simulated BMP or M(t), the amount of biomethane that can be produced, then the energy content of the produced biomethane can be calculated, which can then be translated into electricity or heat based on the electrical and thermal efficiency of the plant (these efficiency values may be inputted by the user or obtained from the database 16).

The simulated AD plant/process outputs based on the feedstock inputs 52a and the AD operational inputs 54b and the generated products (e.g., electricity, heat, bio-methane, biogas, digestate or bio-fertilizer) will feed into the financial model 158 and the greenhouse gas emission model 156.

The financial assessment model 158 receives inputs from the financial model 54d, and the feedstock and AD operational models 152 and 154. The financial assessment model 158 can be customized for the anaerobic digestion process. It includes the analysis (such as net present value for example) to calculate the feedstock financials, plant capital costs, operational costs (including feedstock financials, fuel/product financials) and maintenance costs, along with the investment strategies. The feedstock financial input parameters include the tipping fee, the cost and an option for free-of-cost feedstocks along with their associated transportation costs. The capex and opex analysis may include details related to the anaerobic digestion projects. For example, the capex analysis may include different physical components of the AD process such as pre-processing equipment (e.g. for grinding, sorting, etc.), and post-processing equipment (e.g. for dewatering, drying, etc.). The opex analysis includes variable operational costs which includes various items such as, but not limited to, one or more of labor costs, maintenance costs, and insurance costs, for example.

The greenhouse gas emission model 156 receives inputs from the greenhouse gas emission inputs 54*c*, the feedstock model 152 and the AD operational model 154 to determine the costs or income due to carbon production. In one example embodiment, the greenhouse gas emission model 156 can perform the following actions for an anaerobic digestion process as follows:

1) identify polluting activities in the anaerobic digestion process such as using a landfill, using incineration, or using a type of fuel within the AD plant (e.g. diesel, natural gas, etc.), which may be determined by the greenhouse gas emission model 156 by using an algorithm that accounts for sources and sinks of GHG generation such as burning wood (e.g. source) and reducing transportation distance (e.g. sink);
2) determine the quantity of resources used (e.g. feedstock and fuels), which can be obtained from the feedstock analysis model 152 and the operational model 154;
3) calculate the emissions generated from different pollutants (e.g. CO2, NOX, etc.) based on the emission factors that are associated with using various fuels (e.g. by burning natural gas) and convert them to a carbon dioxide equivalent (CO2eq) by using the "global warming potential" GWP (for example using equation 8); and
4) calculate the total emissions produced and translate this into cost or income based on the carbon credit pricing and the quantity of CO2 generated or saved.

In another example embodiment, the greenhouse gas emission model 156 can determine the CO2eq using equation 8.

$$CO_{2eq} = \text{direct emissions} + \text{indirect emissions} - \text{direct offsets} - \text{avoided emissions} \quad (8)$$

where:
1) direct emissions are emissions related directly to the anaerobic digestion process: (e.g. GHG released from power generation);
2) indirect emissions: are emissions that are a by-product of the AD plant operations (e.g. GHG released from transportation of feedstock);
3) direct offsets: (e.g. GHG avoided from replacing fossil fuel with electricity as a power source); and
4) avoided emissions: (e.g. GHG avoided from the current disposal methods such as landfill, incineration or composting).

Accordingly, the list of activities that may be performed based on the analysis from the greenhouse gas emission model 156 includes one or more of: a) Replacing fossil electricity; b) Replacing natural gas/methane; c) Replacing fossil heat; d) Preventing the emission of landfill gas; e) Reducing the waste collection system (transportation); and f) Replacing the synthetic fertilizer in the agriculture and recycling nutrients. The "replacing" is meant to use "cleaner" inputs that are more environmentally friendly.

It should be noted that in an alternative embodiment the simulations can be performed without using the financial model 158, the greenhouse gas emission model 156, the financial inputs 54*d*, or the greenhouse gas emission inputs 54*d*. In such embodiments, the efficiency of the AD plant operation, the usage of certain input materials, and/or production of certain valuable outputs and/or waste outputs can be determined without using financials. In such embodiments, optimization can also be done to optimize the efficiency of the AD plant operation, for example, with regards to minimizing usage/leftover of certain input materials, maximizing the production of certain valuable outputs and/or minimizing certain waste outputs. Implementation of the optimization process is described in further detail below. For example, maximizing the production of certain valuable inputs may mean that the user wants to maximize the biomethane produced annually. In this case, financial assessment is not needed and the feedstock and process criteria are used by the simulation engine to simulate the biomethane produced within a one year period. As another example, minimizing certain waste outputs may mean minimizing the electrical output while maximizing the biomethane output. The user can customize the simulation criteria as they desire.

Referring again to FIG. 4, at act 116, the results from the simulation can be presented, analyzed and also output (e.g. in report form in a hardcopy, a softcopy or output on a display) for review by the user or another person. For example, the results and the analysis can be displayed on a user interface of the user browser 28 and/or the results and analysis may be included in a report that is generated to show the simulation results. The results can include graphs of certain variables that were measured under certain operating conditions. The analysis and results can be stored in the database 16. The method 100 may then end at act 118.

Alternatively, in another example embodiment, after act 114, the method 100 may optionally include act 120, where the predicted simulation results will be validated using real results for a few characteristics, such as, but not limited to, BMP values, for example, obtained from the same operating facility or experimental data from the literature or other operating facilities (if the operational results are not available). The validation involves determining whether the AD simulation model accurately models the plant during real-life operation by determining whether the difference between the predicted simulation results and the actual or experimental data are smaller than a predefined simulation accuracy threshold.

For example, the BMP values (determined from one or both of the transient and steady state models) obtained from the simulation results may be compared to the actual BMP values obtained from the plant. It should be noted that the validation points are not limited to BMP values and can be changed depending upon the project characteristics and optimization goals (for example, instead of BMP values, the digestate mass flow rate or the digestate total solid may be used). The simulation accuracy threshold can be set to an initial default value, such as but not limited to 1%, 2%, or 5% for example, but users will be able to change this value by providing user input. The simulation accuracy threshold represents a trade off since when more accuracy is required a new set of recipes has to be created more often. This means adjustments are made to the models and more simulations are done in order to increase simulation accuracy, which means that more computation time is used.

Alternatively, in yet another example embodiment, after act 114, the method 100 may optionally include act 122 where the predicted simulation results are sent to the near-line simulator so that the results can be optimized. An example embodiment of a method 200 for performing optimization will be described in more detail with respect to FIG. 6.

Figure 8:
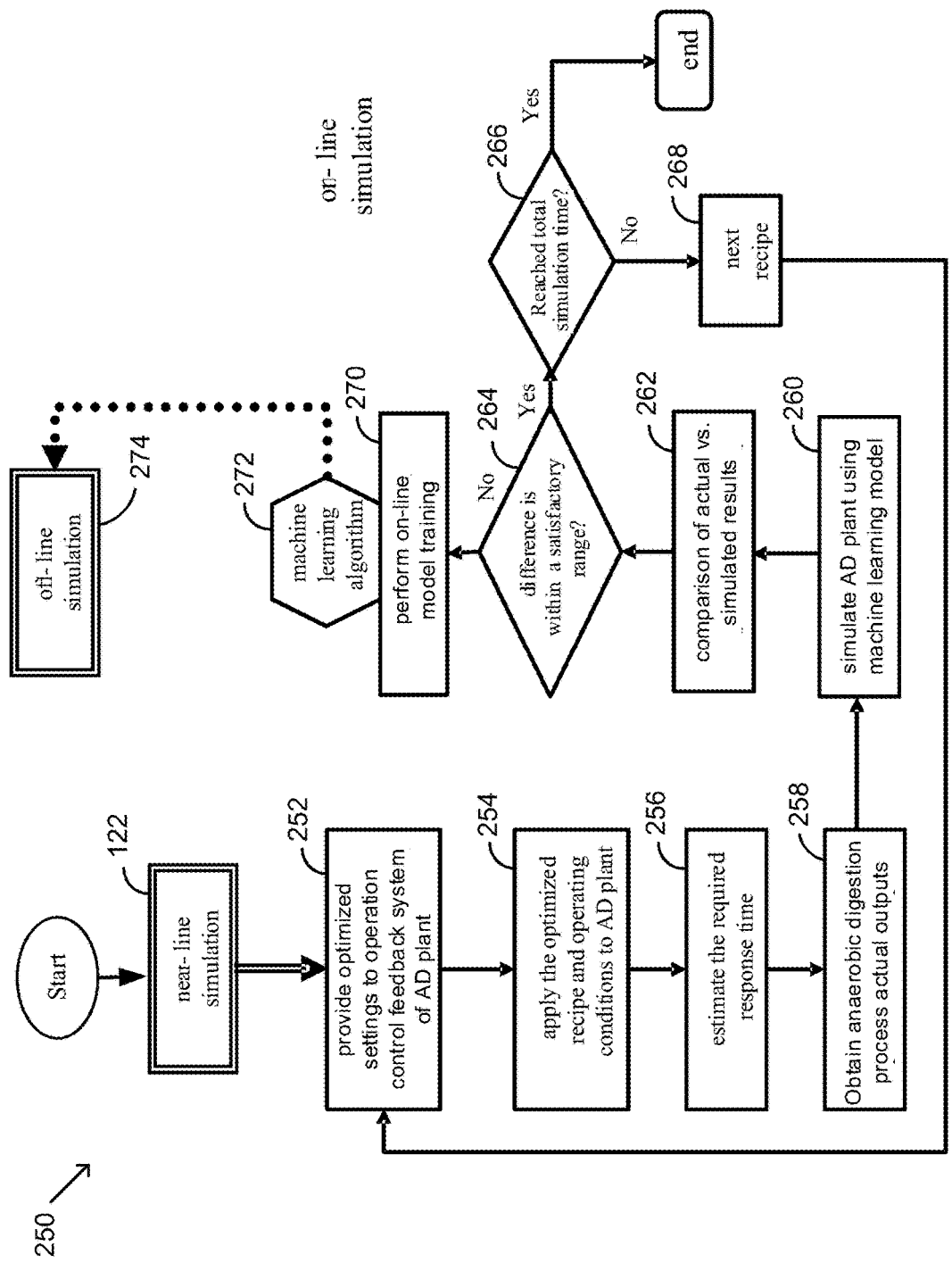
FIG. 8 is a flowchart of an example embodiment of an online simulation method for simulating the operation of the AD plant using machine learning.
Figure 9:
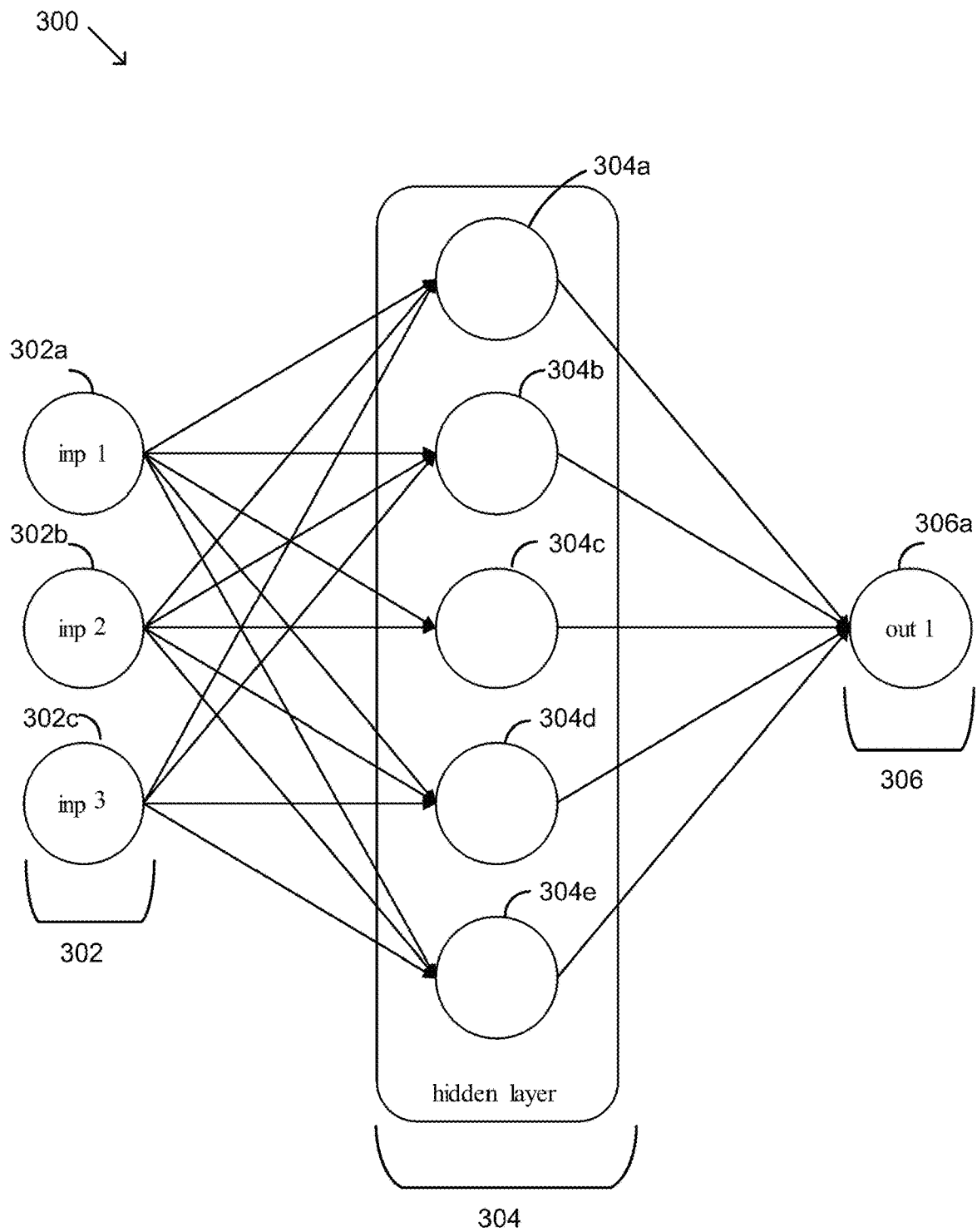
FIG. 9 is an illustration of a neural network topology that can be used by the method of FIG. 8.

Alternatively, in yet another example embodiment, after act 114, the method 100 may optionally include act 124, where the results of the online simulation method (i.e. a machine learning model, an example of which is method 250 in FIG. 8) are used to update the values of the inputs that are used in the simulation at act 114. For example, if the prediction model is completed for a certain time period, but the project inputs change (e.g. feedstock information, financial model etc.) after the time period, the inputs 54 are updated accordingly to prepare for another simulation to be done for the future time period (e.g. the feedstock available for generating the next recipe may be increased or decreased; the type of feedstock is changed for the next recipe; or some characteristics of the feedstock is changed for the next recipe). The updated values for the inputs 54 can also be stored in the database 16. Furthermore, the simulation performed by the machine learning model may provide more accurate simulation results which may be used to adjust the current models that are used by the AD operational simulator. These adjustments may include changing coefficients and/or adding additional terms in equations that are used by the various models until the simulation accuracy of these models is at an acceptable level. These updated models may also be stored in the database 16. In addition, the more accurate simulation results may be stored in the database 16 and used for future validation.

Figure 6:
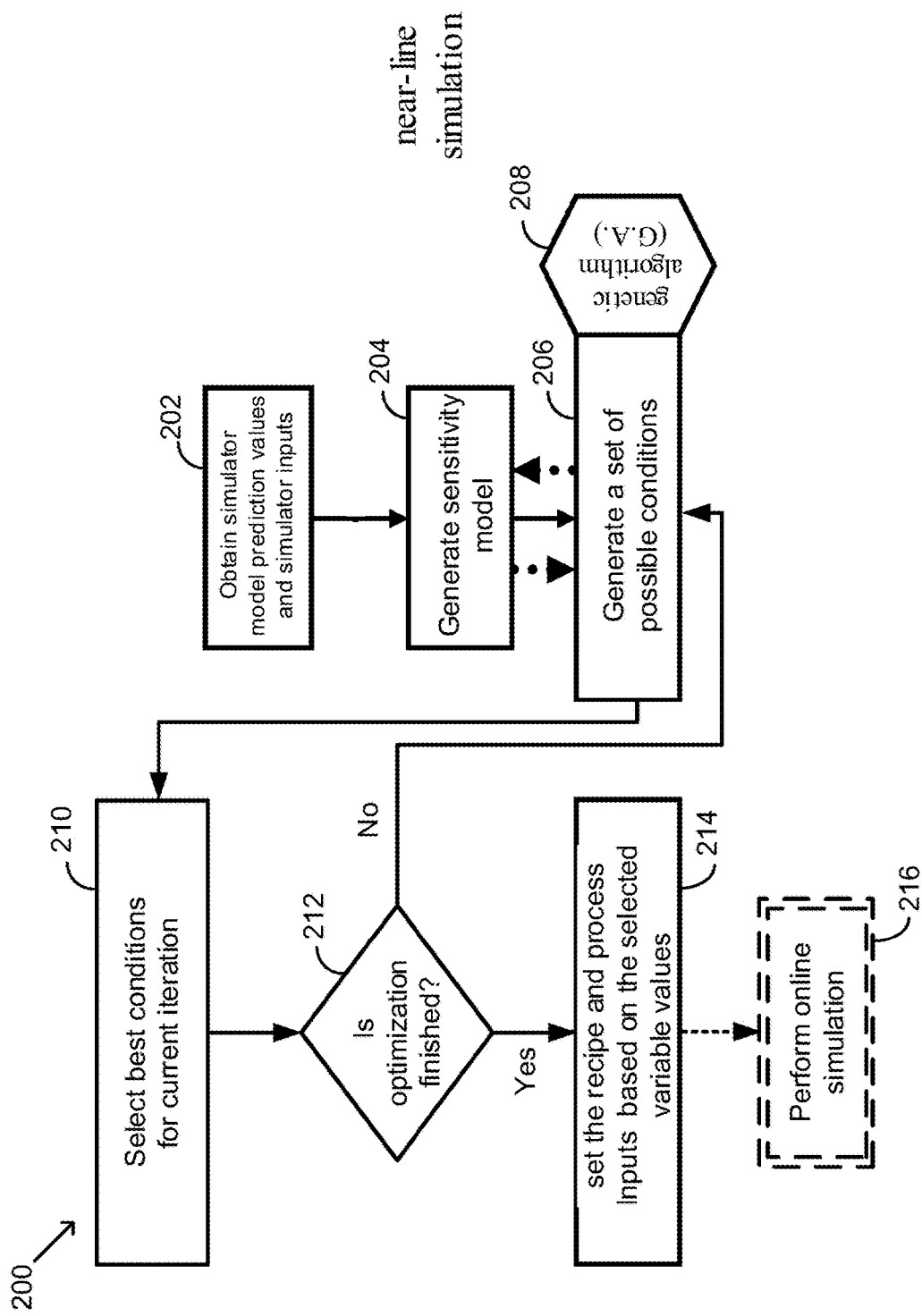
FIG. 6 is a flowchart of an example embodiment of a method for optimizing the operation of an AD plant after its performance has been assessed.

Referring now to FIG. 6, shown therein is a flowchart of an example embodiment of a method 200 for optimizing the operation of an AD plant after its performance has been assessed. The optimization method 200 produces optimal conditions for the quantity of the input materials used over a given time period to create a set of recipes as well as the operational parameters of the AD plant over the given time period. The sets of recipes and operational parameters will be selected as the output of this two-step simulation (i.e. off-line followed by near-line simulation). The results obtained from the two-step simulation may be used for the pre-design assessment of a new anaerobic digestion project. It can also be used for retrofitting of existing AD facilities. This shows the versatility of the simulation methods that are in accordance with the teachings herein.

The method 200 begins at act 202 where the predicted simulator values are obtained from the results of the off-line simulation. In addition, the inputs for the sensitivity and optimization model are obtained. This includes the simulation criteria inputs 54*e* and the optimization criteria 54*f*. The simulation criteria inputs 54*e* may have been specified by the user and may include the variables that were selected for sensitivity analysis, the range over which these variables are varied, and possibly the number of iterations to perform during sensitivity analysis and optimization. Additionally, the threshold for stopping the sensitivity analysis/optimization and/or the amount of time to perform that is allowed for performing the sensitivity analysis is included.

It should be noted that sensitivity analysis can be used for optimization purposes. For example, in at least one embodiment, a deterministic approach, may use the ranked list of most influencing parameters (from the sensitivity analysis) to optimize these parameters first before moving on to optimizing less important parameters.

Part of the optimization process is for the simulation engine 14 to automatically identify high-sensitivity variables in the anaerobic digestion project/plants that influence the viability of the project (i.e. the performance of the project). For example, a given project has a number of inputs that influence the outputs. A correlation measure, such as the Spearman Rank Correlation Coefficient, for example, may be used to process all of the inputs to determine which inputs will have a larger impact on the important outputs defined by the user. Once these variables are determined, they are ranked with the variables having the highest impact (i.e. being the most sensitive) being listed first. These variables are then entered into a recommended list in their ranked order so that the user can pick variables from this list (at act 104 of method 100) for performing sensitivity analysis and determining the optimal operating conditions of the AD plant. This then gives the user the ability to define different sensitivity scenarios by simulating them using the simulation engine 14 (which may also be referred to as a simulation platform) and analyzing and comparing the simulation results.

At act 204, the method 200 generates a sensitivity and optimization model using the sensitivity variables (i.e. the variables with which to perform sensitivity analysis), the values for these sensitivity variables that were determined by the off-line simulation and the ranges over which these variables can vary. The sensitivity and optimization model may also be defined by the number of optimization iterations to perform, a time limit for performing optimization and an optimization threshold that once achieved will stop the optimization.

The method 200 then generates a mesh in a finite N-dimensional space for the sensitivity and optimization model where N is the number of variables chosen for the sensitivity analysis, and the boundary for each variable determines the extent of the mesh along the dimension corresponding to that variable. The number of points along the dimension correspond to a step-size that the user can specify as well as the maximum and minimum values for the variable.

For example, for a 3D mesh, variable X1 can be specified to have a starting value of 10, an ending value of 30 and an interval size of 5 so that variable X1 has the values 10, 15, 20, 25 and 30. Furthermore, variable X2, can be specified to have a starting value of 1, an ending value of 5 and an interval size of 1 so that variable X2 has the values: 1, 2, 3, 4 and 5. A fitness function can then be defined which represents at least one operational goal to be achieved. The fitness function uses one the values of X1, e.g. X1(1), and one of the values of Y1, e.g. Y1(1), to generate a result Z1(1) and these three values then make up one point of the 3D mesh representing the fitness function for the sensitivity and optimization model. Therefore, for N variables over which to perform the optimization, an N-dimensional fitness function is used which generates and N-dimensional mesh. For determining the fitness function, while the number of feedstocks, fuel and the like is changing during simulation, the fitness function can be defined in accordance with the simulation goal (i.e. maximization, minimization, etc.). Alternatively, a machine learning model can be used for the fitness function.

The N-dimensional, finite space can then be explored and evaluated for optimization. Each point in this space requires a computation. Computing each single one of these points even with closed boundaries to find the optimal point (i.e. the optimal scenario) on the N-dimensional mesh may take too much time especially if N is a large number. However, when simply used for presentation purposes, a user can move the sliders for each sensitivity variable to effectively select one point (i.e. a selected scenario) on the N-dimensional mesh instead of generating the whole N-dimensional mesh first. The currently selected scenario can then be scheduled for computation by the computation scheduler 22 and the results can be sent to the user's browser 28 for display in a graph/table or other suitable format. This usually takes less than a second when done for just one scenario, which is very fast considering the time it takes to load data using an internet or network connection. However, the problem is that this is random in that the user has to select a high number of points in order to try to find the best scenario (i.e. optimal operating conditions) and this may therefore also result in a very long computational time due to the user using trial and error in selecting the points for computation which makes this an impractical way of performing optimization. Method 200 overcomes this problem by iteratively selecting a number of points on the N-dimensional mesh in order to find a global maximum or minimum that represents the optimal scenario. The initial points are randomly created within parameter ranges provided by the user.

At act 206, the method 200 evaluates a set of possible conditions. In some embodiments, these conditions can be generated using a brute force deterministic technique where each possible combination of values for the input variables are used for computation and the best result (for achieving the optimization goal) is one chosen. Alternatively, a more preferable approach may be to use a Genetic Algorithm (GA) to determine the conditions.

In embodiments in which the deterministic approach is used, only one of the N-variables is varied at a time by increasing or decreasing its value along a current variable's dimension based on the step-size and the starting and ending values for that current variable while keeping the other variables constant. This is done until the best possible value is found for the current variable before moving onto the next variable. However, this technique may also be very computationally intensive as this requires many conditions to be iteratively generated in order to find a global maximum or minimum that represents the optimal condition. Computing all possible values has a very high complexity requiring NAN computations in order to check every possible combination in the N-dimensional space. Furthermore, if this technique is run for a subset of the NAN combinations of computations then this technique may end up finding conditions that are local maximums or local minimums rather than finding the most optimal global maximum or minimum condition.

In embodiments in which the GA is used to explore the N-dimensional space for optimization purposes, at act 208 the GA generates a random set of M points within this bounded N-dimensional space. Each of these M points represents a different condition for the AD plant meaning a different set of values for the input variables (i.e. different feedstock values (such as quantity) and a different set of operational values for the AD plant).

The optimization method 200 then moves to act 210 where a fitness function is used to evaluate the M points to determine M results. The fitness function is defined based on the goal that is being achieved, i.e. a goal may be to maximize an output such as electricity or methane production or minimize an output such as greenhouse gas emissions, for example. After the M points are evaluated using the fitness function to obtain M results, a probability score is generated based on the M results to determine which of the M points are more likely to be closer to the optimal condition. The probability scores of the M points are then used to rank the M points. The P higher ranked points have a higher chance of being closer to the optimal condition and are selected as being the best conditions for the next iteration of the process. The value P, which is the number of potential solutions in each generation, can be predefined and selected so that the computational time for performing optimization is within a desired time limit. A cross-mutation may then be applied to the P higher ranked points to generate the starting points for the next iteration of optimization.

The fitness function can be determined based on an optimization goal. The feedstock amounts and characteristics in combination with the process metrics are used for an algorithm modeling the biological processes in the digester to calculate the amount of biogas and digestate that are produced. Using these values, all other products and the financial aspects are computed. Alternatively, the fitness function can be determined based on the simulation results by training a machine learning model that takes the previously mentioned inputs, such as feedstock parameters and process variables, and processes them to predict the output products. For example, during early operation of the simulation engine 14 on a new project, the fitness function can be generated from certain equations used by the models in the anaerobic digestion simulator. However, as the machine learning model evolves to provide more accurate simulation performance then the machine learning model may be used as the fitness function.

When machine learning is used, the feedback of each optimization process influences the fitness-function. For example, the fitness function may be a training based algorithm that is similar to a neural network used by the machine learning model for performing an off-line simulation of the operation of the AD plant. Real life results are compared to the simulator model predictions and the dataset is added to the training data set if the error is too high in order to tune the machine learning model to improve its performance. Likewise the fitness function may also get tuned over time for improved performance. This may be done by adjusting the constant factors used in the model for determining the amounts of biogas and digestate to fit more closely with actual results.

The optimization method 200 then moves to act 212 where it is determined whether another iteration is to be performed. If so, the optimization method 200 moves to acts 206, 208 and 210 where the process of evaluating the M points with the fitness function to obtain the M results, determining probability scores using the M results and then performing the cross-mutation operation to generate a new set of M points is repeated until the incremental results from the fitness function for a given iteration is below a predefined threshold or a predefined computation time has been reached for optimization at which point the optimization method 200 moves to act 214. The incremental results of a given iteration being below the predefined threshold means that the difference of the best result (i.e. highest or lowest result depending on whether maximizing or minimizing a goal) for the given iteration compared to the best result from a previous iteration, or the average of the best results of several previous iterations is lower than the predefined threshold.

If at act 212 it is determined that another optimization iteration is to be performed then the optimization method 200 moves to act 206 where in the next iteration of this process, another set of M points is generated. The M points for the next iteration may be created by taking the selected data points (i.e. operating points) from the current iteration, and cross-mutating them to create new parameter sets (i.e. a collection of potential operating or data points) based on picking different variables from each of the selected data points and combining them together in forming a new data point. Each pair of old data points for creating a new data point is selected based on their performance in the previous iteration. This is done in order to create a new set of M data points in which the data points are moved closer to the optimal condition. The randomness at the first iteration of this technique helps the optimization method 200 to reach a global maximum or global minimum and therefore reach the optimum condition rather than reaching a local maximum or minimum.

It should be noted that during this iterative process, when a new set of possible operating conditions (i.e. data points) is generated this has an effect on the sensitivity and optimization model as some of the variables may change in value compared to the value determined during the off-line simulation. For example, an input material may be used up. Accordingly, the values for certain variables in the sensitivity and optimization model are updated such that there is a loop between acts 204, 206 and 208 of the optimization method 200 represented by the dashed arrows in FIG. 6.

Once the iterative process has ended, the optimization method 200 moves to act 214, where the optimal values for the variables that are most likely to influence the operation of the AD plant are selected and saved in the database 16. These optimal values may also be referred to as the on-line simulation predictions. It should be noted that these optimal values include a set of K recipes and a set of K operational values when the simulation is being performed over K intervals. It should be recalled that the availability of the feedstock materials can change over time and so this is taken into account by operating the AD plant over K intervals and noting the change in feedstock supply over each of the K time intervals. This change over each interval may dictate different operating conditions for the AD plant for different time intervals so that it performs optimally with respect to some desired goal where one or more operating parameters are being maximized and/or minimized. The time interval may be set to be the Hydraulic Retention Time (HRT), which is the amount of time that it takes the digester to use up a mixture of feedstock materials. Alternatively, the time interval may be specified by the user to be a different unit of time such as a number of days, a number of weeks, a number of months, or a number of years, for example.

At act 216, the optimization method 200 may optionally proceed to perform the third stage of the simulation, which is the online simulation. Alternatively, the optimization method 200 may end at act 214 and the results of the optimization can be analyzed and included in a report or shown on a display to the user.

Figure 7:
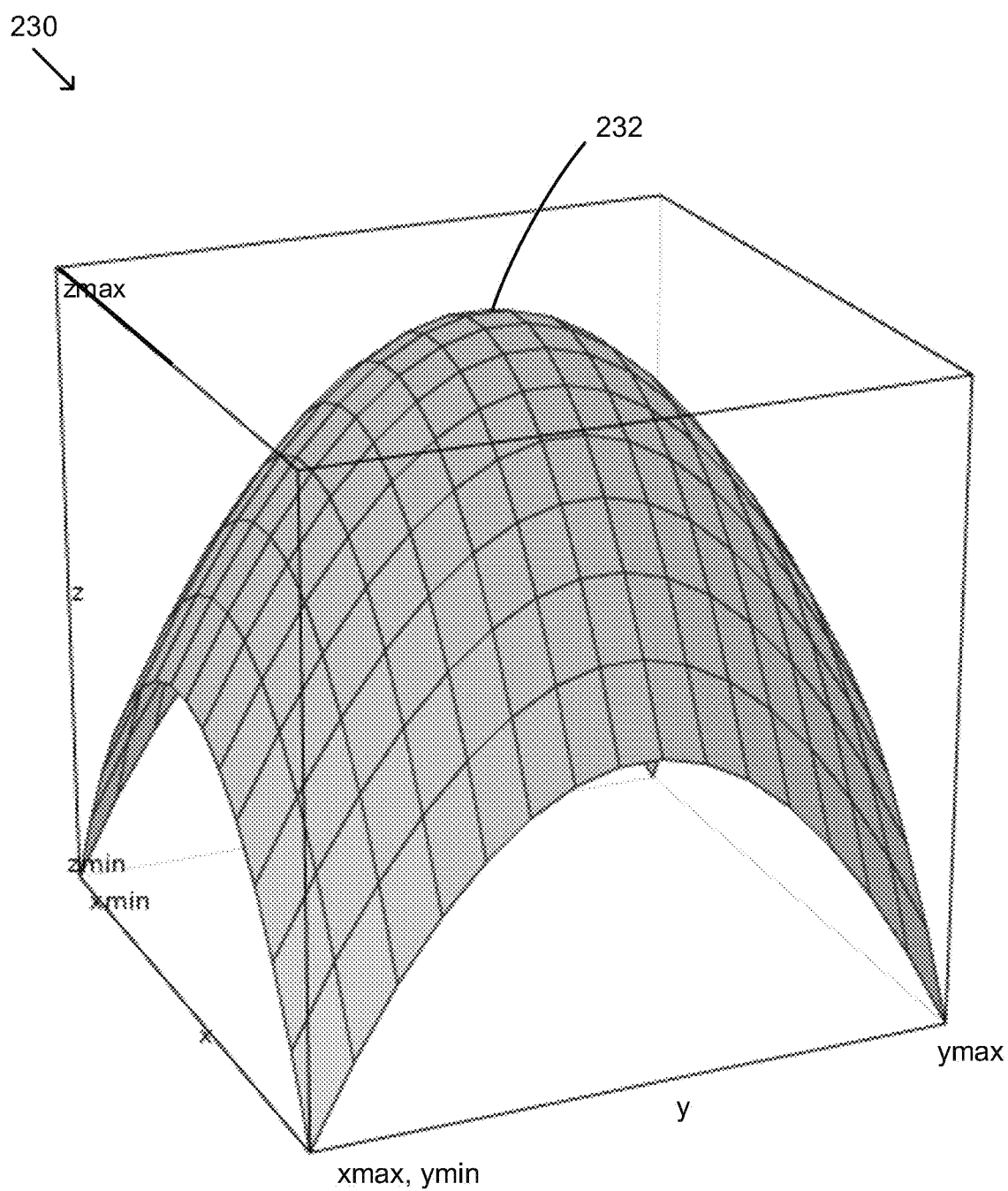
FIG. 7 is an illustration showing an example of an N-dimensional mesh that is generated during optimization using a genetic algorithm.

Referring now to FIG. 7, shown therein is an illustration of an example of a 3-dimensional mesh 230 that is generated during optimization using the GA. In this case, there are two variables x and y and one result variable z. The bounded space for the mesh 230 is generated based on the ranges of +/−50 for both the x and y variables (although they don't have to have the same range in general). The result z is determined based on applying a fitness function to sets of (x, y) points.

This example assumes:
using a fitness function $z=f(x, y)=-3x^2-3y^2$,
the optimal condition is a global maximum at (0, 0) with $f(0,0)=0$ in the example shown;
a randomly generated set of points is obtained in the first iteration (i.e. Generation 0) as:
G0={A0=(−7, 8), B0=(−5, 5), C0=(24, 27), D0=(−41, −13), E0=(33, −13)}; and the first set of result values obtained for each point in G0 are:
R0={−339, −150, −3815, −5550, −3774}.

In order to create the next generation of points (i.e. conditions) for the next iteration, the performance of each tuple (i.e. data point) is considered based on the probability of selecting that particular point. In the first iteration of this example the best result was −150 and probabilities for selecting the data points may be determined by obtaining probability scores by multiplying the worst result (i.e. −5550) by −1, adjusting each result by adding the multiplied value to each result, summing the adjusted values to obtain a sum and then dividing the initial results by the sum to obtain the probabilities (rounded to the second digit after the decimal point):
P0={0.37, 0.38, 0.11, 0, 0.12}.
It should be noted that other ways of determining the probability score can be used in other embodiments and this is just one example.

Using the probability scores, the points are ranked and 5 new pairings are created by applying a cross function to the P top ranked points (in this example P=3). The pairings chosen by the cross function for this example are:
S1={(C0, B0), (B0, C0), (C0, A0), (B0, A0), (E0, B0)}.
The likelihood of a data point from the previous iteration being selected is based on the probabilities found in P0. As point D had a probability of 0, it has not been selected for the creation of any data point for the next iteration while points A0 and B0 are selected more frequently based on their high probability values (37% and 38% respectively).

For each of these data points, the pairings are then combined to result in the following set for the next iteration (i.e. Generation 1) of data points (rounded to the second digit after the decimal point):
G1={A1=(1.74, 10.11), B1=(17.26, 10.11), C1=(16.8, 12.42), D1=(−6.54, 7.3), E1(3.83, 0.82)},
where the pairings are combined according to a certain function, which in this example was a weighted average using the probability scores as follows:

$$X\_A1=(X\_C0*C\_P0+X\_B0*B\_P0)/(B\_P0+C\_P0),$$

where X_A1 is the x coordinate of data point A1, X_C0 is the x coordinate of data point C0, C_P0 is the probability score for data point C0, X_B0 is the x coordinate of data point B0 and B_P0 is the probability score for data point B0. However, in other embodiments, other types of functions can be used to combine the coordinates of the higher ranked P selected data points to come up with the coordinates for the P data points in the next generation (i.e. next iteration).

The fitness function is then applied to the next generation of data points to come up with the next generation of results, which in this example is as follows:
R1={−315, −1200.55, −1308.70, −288.12, −46.04}.
From this example, it can be seen that the best result changed from −150 (in the first generation G0) to −46 (in the next generation G1) while the rest of the numbers are also getting closer to the global maximum in this case which is at $f(0,0)=0$.

This technique is then iteratively applied to continue this trend and leads to a continuous reduction between the best and worst result while approaching the maximum value in the mesh. Doing this in quick succession results in a high accuracy after a short period of time. This optimization technique can be extended to use a high number of parameters and any fitness function which replaces f(x, y) of the example.

In alternative embodiments, different cross-mutation functions (also referred to as crossing functions) can be used depending on the variable types that are used for optimization where variable types relate to the format of the values of the variables which can include integer, floating point, etc. Furthermore, when selecting the best data points for a current iteration from which to create the data points for the next iteration/generation of the GA, survival of the fittest may be used where only the data point associated with the best result is taken or another method may be used where the only data point associated with the worst result is dropped.

Referring now to FIG. 8, shown therein is a flowchart of an example embodiment of an online simulation method 250 for simulating the operation of the AD plant using machine learning for a given time interval of the overall simulation time period. In method 250, real data from an AD plant that is operated based on the optimized settings (i.e. the optimized recipe(s) and operating conditions) will be compared to simulator model predictions when operating the machine learning model using the same optimized settings to determine if any of the models (e.g. one or more of the steady state feedstock model 152a, the transient feedstock model 152b, the AD operational model 154, the greenhouse gas emission model 156 or the financial assessment model 158) used by the simulation engine 14 need to be adjusted to simulate real-world results more accurately.

At act 252, the optimized settings from the two-step simulation of the off-line and near-line simulations 122 are provided to the plant controller 30 for an actual AD plant. At act 254, the optimized settings are applied to the real (i.e. actual physical) AD plant. This includes implementing the optimized recipe for the current time period of operation (e.g. the current HRT) as well as the corresponding operational plant settings.

After the implementation at act 254, the method 250 proceeds to act 256, where the required response time will be estimated, which is the expected response time which is the time duration that it will take the AD plant to show the desired operational goals (i.e. maximization or minimization of certain material usage or product creation or other optimization goals as described previously), which can also be referred to as the "possible response". This response time can be estimated based on the HRT, the flow of the feedstock materials, the digester volume and the operational conditions. As an initial condition, the response time can be the HRT and the estimated response time may then be improved based on the simulated results obtained from the plant during the process (e.g. sensory values, intermediate outputs, etc.).

The method 250 then proceeds to act 258, where the actual results from the actual AD plant are obtained when the response time has elapsed. These results can be referred to as the anaerobic digestion process actual outputs and these results can be obtained in real-time using various sensors, such as, but not limited to energy output, biomethane gas flow, and temperature sensors, for example, at the AD plant. In alternative embodiments, the results can also be obtained at time intervals that are smaller than the response time to see how the actual AD process performs over time.

The method 250 then moves to act 260 where the machine learning model is operated using the same optimized settings to generate the online simulation predictions. Using the neural network topology of FIG. 9 as an example, the machine learning model may be a neural network 300 with an input layer 302 having a number of input nodes (302a to 302c) that may be equal to the number of input parameters that are used by the off-line simulation method. The input nodes 302a to 302c are linked into a first intermediate layer (i.e. hidden stage) 304 that has a number of internal nodes 304a to 304e that are each connected to all of the input nodes 302a to 302c. The number of hidden layers 304 is generally greater than 0, but might be zero in some extreme cases, and each hidden layer treats the previous hidden layer as an input layer. All inputs are connected to at least one of the hidden layer nodes and when some inputs are not needed they are given a weight of zero or a very small weight. The internal nodes of the last hidden layer are then connected to the output nodes in the output layer 306 for the desired output. If only one metric is computed (i.e. there is only one desired goal such as maximizing a parameter value, minimizing a parameter value or a combination of maximizing and minimizing different parameter values as explained previously), then there is only one output node 306a for the machine learning model. With this topology, the input layer and the output layer are visible layers. It should be noted that the neural network used in the machine learning model can have different topologies, a different number of input nodes, a different number of intermediate nodes, a different number of hidden layers and/or a different number of output nodes compared to the example shown in FIG. 9.

Once the structure is set, each intermediate node uses the input nodes and generates its own output. As an example, a given intermediate node can generate its own output by applying weights to scale the values that are provided by the input nodes that it is connected to and then applying one or more functions, which may be nonlinear, to the scaled inputs to obtain outputs which can then be added or subtracted from one another to obtain the final output. The exact behavior of a given node can be changed based on a training stage where inputs and desired outputs are used to create such changes. The training uses training data that are observed from the actual operation of a plant (i.e. actual inputs and outputs observed during plant operation). The training also uses training data that can be created using simulation (i.e. with deterministic fitness functions and random input values). For example, a random plant scenario is created and the formulas of the models described herein are applied. The combination of (all relevant) inputs and the computed output is one training data point. An arbitrary number of such training data points can be generated. The inputs can include feedstock, fuel and operating parameters (see FIG. 3 and the related description). At the beginning of training, the intermediate nodes change the input manipulation randomly. However, as each new training set is used to train the machine learning model, the intermediate nodes change the input manipulation incrementally until the expected result is reached. This means that once training is finished, when the training sets are applied to the neural network, the neural network will always produce the expected result. The machine learning model is built and trained to obtain an initial machine learning model.

The optimized recipe and operational settings are applied to the initial machine learning model to generate the simulator model predicted results at act 260 when the online simulation method 250 is first operated for a given AD plant. However, as the online simulation method 250 is operated on more and more actual data points from the AD plant, the machine learning model is continuously improved as is described with respect to acts 262 and 264 below.

At act 262, all of the simulator model predicted results are compared to the actual outcomes of the real-life AD plant to determine a prediction error by looking at some measure such as, but not limited to, absolute difference, mean square error, root mean squared error, etc., of the difference between the predicted and actual results.

At act 264, the method 250 determines whether the prediction error is within an acceptable range. The acceptable range depends on the output parameter that is produced by the simulation. The acceptable range can be a low percentage of change between consecutive simulations, a low absolute change in value between consecutive simulations, or the amount of time that passed since the initial computations for the simulation were performed. Should the prediction error be too high, the method 250 proceeds to act 270 where the newly gained data set from actual operation of the AD plant can be added to the training data and saved in the database 16 and the machine learning model undergoes further training in order to improve the accuracy of the overall computation. Once the machine learning model is further trained, the new manipulations provided by the internal nodes are saved for the machine learning model at 272.

The method 250 then proceeds to act 274, where the updated results may be applied to the off-line simulator so that the models used by the off-line simulator can be adjusted for performing more accurate near-line simulations. These adjustments may include changing coefficients and/or adding terms for these equations used by the various models of the anaerobic digest simulator. The two-step simulation can then also be re-run to obtain updated optimized values for the recipes (i.e. input feedstocks) and the operational conditions after which, the entire three-step simulation will be repeated. The real-time data obtained from the AD plant may also be used for improving the validation of the near-line simulator and also updating the values in the database 16 for that specific facility as shown in FIG. 4. This feedback loop may be used throughout the lifetime of the simulation engine 14 in order to continuously improve the accuracy of the machine learning model that is being used for simulations.

Returning back to act 264, if the difference between the actual results and the predicted results is within the satisfactory range, then the current optimized settings will continue to be used. The method 250 then proceeds to act 266 where it is determined whether the total simulation time has been reached. If this determination is true then the method 250 ends.

If the determination at act 266 is not true, then the recipe will continue to be applied as planned, and the method 250 proceeds to act 268 where the next recipe, i.e. for the next simulation iteration for the next time interval is selected and provided to the operation control feedback system of the AD plant at act 252 and another iteration of acts 254 to 264 is performed and acts 270 to 274 may also be performed if the error of the predicted results is larger than the error threshold.

It should be noted that while the teachings herein have been described with reference to an AD plant, the teachings herein can be applied to other types of plants that use other processes. This can be done by identifying the input parameters of each system and developing corresponding model representations for each of them. For example, the methodologies described herein can be applied to various technologies including, but not limited to, Pyrolysis, Torrefaction and Gasification. The simulation and optimization structures can therefore be applied to those models with minor adjustments.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

[1] Lesteur, M., Bellon-Maurel, V., Gonzalez, C., Latrille, E., Roger, J. M., Junqua, G., Steyer, J. P., "Alternative methods for determining anaerobic biodegradability: A review", Process Biochemistry, Volume 45, Issue 4, April 2010, pp. 431-440.

[2] Raposo, F., Fernandez-Cegri, V., De la Rubia, M. A., Borja, R., Beline, F., Cavinato, C., Demirer, G., Fernandez, B., Fernandez-Polanco, M., Frigon, J. C., Ganesh, R., Kaparaju, P., Koubova, J., Mendez, R., Menin, G., Peene, A., Sherer, P., Torrijos, M., Uellendahl, H., Wierinck, I., de Wilde, V., "Biochemical methane potential (BMP) of solid organic substrates: evaluation of anaerobic biodegradability using data from an international interlaboratory study", Journal of Chemical Technology, Volume 86, Issue 8, August 2011, pp. 1088-1098.

[3] Tarvin, D., and Buswell, A. M., "The Methane Fermentation of Organic Acids and Carbohydrates", Journal of the American Chemical Society, 1934, 56 (8), pp. 1751-1755.

[4] Dennehy, C., Lawlor, P. G., Croize, T., Jiang, Y., Morrison, L., Gardiner, G. E., Zhan, X., 2016. Synergism and effect of high initial volatile fatty acid concentrations during food waste and pig manure anaerobic co-digestion. Waste Manage. 56, 173-180.

[5] Kafle, G. K., Chen, L., 2016. Comparison on batch anaerobic digestion of five different livestock manures and prediction of biochemical methane potential (BMP) using different statistical models. Waste Manage. 48, 492-502.

[6] Xie, S., Lawlor, P. G., Frost, J. P., Hu, Z., Zhan, X., 2011. Effect of pig manure to grass silage ratio on methane production in batch anaerobic co-digestion of concentrated pig manure and grass silage. Bioresour. Technol. 102 (10), 5728-5733.

[7] Ma, J., Yu, L., Frear, C., Zhao, Q., Li, X., Chen, S., 2013. Kinetics of psychrophilic anaerobic sequencing batch reactor treating flushed dairy manure. Bioresour. Technol. 131, 6-12.

[8] Zhao, C., Yan, H., Liu, Y., Huang, Y., Zhang, R., Chen, C., Liu, G., 2016. Bio-energy conversion performance, biodegradability, and kinetic analysis of different fruit residues during discontinuous anaerobic digestion. Waste Manage.

[9] Rao, M. S., Singh, S. P., Singh, A. K., Sodha, M. S., 2000. Bioenergy conversion studies of the organic fraction of MSW: assessment of ultimate bioenergy production potential of municipal garbage. Appl. Energy 66 (1), 75-87.

The invention claimed is:

1. A system for performing at least one of assessing, optimizing and/or controlling the performance of an Anaerobic Digestion (AD) plant, wherein the system comprises:
a user interface for allowing a user to enter user inputs to define various aspects of the AD plant operation and to view results of the simulation;
a database for storing inputs used for the simulation and/or optimization of the anaerobic digestion plant, the inputs including feedstock inputs, AD operational inputs, and simulation criteria; and a server that controls the operation of the system and generates the user interface, the server being configured to operate a simulation engine according to a three stage process including an off-line simulation mode, a near-line simulation mode and an online simulation mode, wherein the simulation engine is configured to:
execute the offline simulation mode to perform a simulation using an Anaerobic Digestion (AD) operational model that includes several models for modelling several aspects of the AD plant operation and generating off-line simulator predictions of the AD plant operation for assessing the performance of the AD plant;
execute the near-line simulation mode which uses the off-line simulator predictions for determining an optimal operating point based on at least one optimization goal and possible scenarios to optimize the performance of the AD plant; and
execute the online simulation mode to simulate the AD plant operation by using machine learning and the optimal operating point to generate online simulator predictions, to generate error results by comparing the online simulator predictions to actual results from the AD plant operation and provide feedback based on the error results where the feedback is used to improve simulation accuracy of one or more of the several models used in the off-line simulation.

2. The system of claim 1, wherein the simulation engine is configured to:
generate an overall biochemical methane potential (BMP) for the AD plant by using a feedstock model and the feedstock inputs; and
generate estimates of biomethane, electricity, and thermal production of the AD plant for a simulated time interval by using the AD operational model and the AD operational inputs, the feedstock inputs and the overall BMP;
where the off-line simulator predictions indicate the operational performance of the AD plant and include the overall BMP, and the estimates of biomethane, electrical and thermal production of the AD plant.

3. The system of claim 2, wherein the feedstock model includes at least one steady state equation for determining the overall BMP or the feedstock model includes at least one transient sub-model for determining a cumulative methane yield.

4. The system of claim 3, wherein the feedstock model includes the at least one steady state equation for determining the overall BMP and the at least one steady state equation determines at least one of a first BMP value due to chemical oxygen demand, a second BMP value due to elemental composition (EC) and a third BMP value due to organic fraction composition, wherein the BMP values are averaged when more than one BMP value is determined.

5. The system of claim 3, wherein the feedstock model includes the at least one transient sub-model for determining the cumulative methane yield and the at least one transient sub-model for determining a cumulative methane yield includes at least one of a first order kinetic model, a Chen and Hashimoto model, a Modified Gompertz model, and a dual pooled first order kinetic model, wherein outputs of the sub-models are averaged when at least two sub-models are used to determine the cumulative methane yield.

6. The system of claim 1, wherein the AD operational model, a financial model, and a greenhouse gas (GHG) emission model are used to generate estimates of biomethane, electricity, bio-fertilizer, thermal production, inflows and outflows of a digester of the AD plant, mass balance, carbon credit pricing, cash flow, income and costs of the AD plant by using BMP models, a digester equation, a biofertilizer equation and a digestate equation based on volume of the inflows and the outflows of the digester of the AD plant and mass balance equations.

7. The system of claim 1, wherein the database further comprises optimization criteria and the simulation engine is further configured to operate the simulation engine in the near-line simulation mode for determining the optimal operating point to optimize the performance of the AD plant with respect to the at least one optimization goal, the optimal operating point, one or more recipes and AD plant operational settings.

8. The system of claim 7, wherein the simulation engine uses a sensitivity analysis and optimization model for performing optimization during the near-line simulation mode where the sensitivity analysis and optimization model includes a set of N input variables that have an influence for achieving the at least one optimization goal, an operating value for each input variable determined from the off-line simulation and a range over which the input variables are varied to define an N-dimensional mesh where the actual optimal operating point is a global maximum or a global minimum of the N-dimensional mesh corresponding to the at least one optimization goal.

9. The system of claim 8, wherein the at least optimization goal comprises maximizing biogas production, maximizing electricity production, minimizing greenhouse gas emissions, and minimizing feedstock leftover or a weighted combination of those options.

10. The system of claim 8, wherein the simulation engine is configured to iteratively generate a set of operating points along the mesh until the optimal operating point is found, which is one of the operating points that is closest to the actual optimal operating point or an operating point that is closest to the at least one optimization goal when an optimization time limit is reached.

11. The system of claim 10, wherein the simulation engine is configured to use a genetic algorithm to randomly generate a first set of operating points, apply a fitness function to the set of operating points to obtain a set of results, determine a probability score for each result to indicate how likely each corresponding operating point is to being nearest to the actual optimal operating point; select a subset of the operating points that have a higher probability score, cross-mutate the selected operating points to generate a new set of operating points and repeat the applying, determining, selecting and cross-mutating steps until one of the optimal operating point is found that is closest to the actual optimal operating point or the operating point with the best result is found when optimization time limit is reached.

12. The system of claim 10, wherein the optimal operating point is sent to a plant controller that controls the operation of the AD plant, where the optimal operating point includes a recipe and operational plant settings for a given time interval of the simulation.

13. The system of claim 12, wherein the simulation engine is further configured to operate in an online simulation mode where a machine learning model is used to simulate the operation of the AD plant to generate online simulator predictions, to compare the online simulator predictions to actual results from the AD plant and to send the plant controller subsequent recipes for the optimal operation of the AD plant for subsequent time intervals.

14. The system of claim 7, wherein in the online simulation mode a machine learning model is used to simulate the AD plant operation to generate the online simulator predictions, compare the online simulator predictions to actual results from the AD plant to determine a simulation error and adjust the machine learning model, the models used for near-line simulation and the values of some of the input variables to improve simulation performance when the simulation error is larger than an error threshold.

15. The system of claim 14, wherein the simulation engine is configured to perform the off-line and near-line simulations before the next online simulation in order to provide the online simulator with an updated optimal operating point for online simulation.

16. A method for performing at least one of assessing, optimizing and/or controlling the performance of an Anaerobic Digestion (AD) plant, wherein the method comprises:
using a server to provide a user interface for allowing a user to enter user inputs to define various aspects of the AD plant operation and to view results of the simulation;
storing inputs in a database where the inputs are used for the simulation of the anaerobic digestion plant, the inputs including feedstock inputs, AD operational inputs, and simulation criteria; and
using the server to generate the user interface and operate a simulation engine according to a three stage process including an off-line simulation mode, a near-line simulation mode and an online simulation mode, where:
the offline simulation mode involves performing a simulation using an Anaerobic Digestion (AD) operational model that includes several models for modelling several aspects of the AD plant operation and generating off-line simulator predictions of the AD plant operation for assessing the performance of the AD plant;
the near-line simulation mode involves using the off-line simulator predictions for determining an optimal operating point based on at least one optimization goal and possible scenarios to optimize the performance of the AD plant; and
the online simulation mode involves simulating the AD plant operation by using machine learning and the optimal operating point to generate online simulator predictions, to generate error results by comparing the online simulator predictions to actual results from the AD plant operation and provide feedback based on the error results where the feedback is used to improve simulation accuracy of one or more of the several models used in the off-line simulation.

17. The method of claim 16, wherein the method comprises operating a simulation engine in the off-line simulation mode for generating the off-line simulator predictions of the AD plant operation by:
using a feedstock model for receiving the feedstock inputs and generating an overall biochemical methane potential (BMP) for the AD plant; and
using the AD operational model for receiving the AD operational inputs, the feedstock inputs and the overall BMP and generating estimates of biomethane, electricity, and thermal production of the AD plant for a simulated time interval,
where the off-line simulator predictions indicate the operational performance of the AD plant and include the overall BMP, and the estimates of biomethane, electrical and thermal production of the AD plant.

18. The method of claim 17, wherein the method comprises using at least one steady state equation for determining the overall BMP or using at least one transient sub-model for determining a cumulative methane yield.

19. The method of claim 16, wherein the method comprises using the at least one steady state equation for determining the overall BMP and the method further comprises determining at least one of a first BMP value due to chemical oxygen demand, a second BMP value due to elemental composition (EC) and a third BMP value due to organic fraction composition, wherein the BMP values are averaged when more than one BMP value is determined.

20. The method of claim 16, wherein the method comprises using the at least one transient sub-model for determining the cumulative methane yield and the method comprises determining the cumulative methane yield by using at least one of a first order kinetic model, a Chen and Hashimoto model, a Modified Gompertz model, and a dual pooled first order kinetic model, wherein outputs of the sub-models are averaged when at least two sub-models are used to determine the cumulative methane yield.

21. The method of claim 16, wherein the method further comprises using the AD operational model, a financial model, and a greenhouse gas emission (GHG) model to generate the estimates of bio-methane, electricity, bio-fertilizer, thermal production, inflows and outflows of a digester of the AD plant, mass balance, carbon credit pricing, cash flow, income and costs of the AD plant by using BMP models, a digester equation, a biofertilizer equation and a digestate equation based on volume of the inflows and the outflows of the digester of the AD plant and mass balance equations.

22. The method of claim 16, wherein the database further comprises optimization criteria and the method comprises operating the simulation engine in the near-line simulation mode for determining the optimal operating point to optimize the performance of the AD plant with respect to the at least one optimization goal, the optimal operating point, one or more recipes and AD plant operational settings.

23. The method of claim 22, wherein the method further comprises using a sensitivity analysis and optimization model during optimization during the near-line simulation mode where the sensitivity analysis and optimization model includes a set of N input variables that have an influence for achieving the at least one optimization goal, an operating value for each input variable determined from the off-line simulation and a range over which the input variables are varied to define an N-dimensional mesh where the actual optimal operating point is a global maximum or a global minimum of the N-dimensional mesh corresponding to the at least one optimization goal.

24. The method of claim 23, wherein the method comprises operating the simulation engine for iteratively generating a set of operating points along the mesh until the optimal operating point is found which is one of the operating points that is closest to the actual optimal operating point or an operating point that is closest to the at least one optimization goal when an optimization time limit is reached.

25. The method of claim 24, wherein the method comprises operating the simulation engine for using a genetic algorithm to randomly generate a first set of operating points, applying a fitness function to the set of operating points to obtain a set of results, determining a probability score for each result to indicate how likely each corresponding operating point is to being nearest to the actual optimal operating point; selecting a subset of the operating points that have a higher probability score, cross-mutating the selected operating points to generate a new set of operating points and repeating the applying, determining, selecting and cross-mutating until one of the optimal operating point is found that is closest to the actual optimal operating point or is the operating point with the best result is found when optimization time limit is reached.

26. The method of claim 23, wherein the method comprises sending the optimal operating point to a plant controller that controls the operation of the AD plant, where the optimal operating point includes a recipe and operational plant settings for a given time interval of the simulation.

27. The method of claim 26, wherein the method comprises operating the simulation engine in an online simulation mode where a machine learning model is used for simulating the operation of the AD plant to generate online simulator predictions, comparing the online simulator predictions to actual results from the AD plant and sending the plant controller subsequent recipes for the optimal operation of the AD plant for subsequent time intervals.

28. The method of claim 22, wherein in the online simulation mode a machine learning model is used for simulating the AD plant operation to generate the online simulator predictions, the online simulator predictions are compared to the actual results from the AD plant to determine a simulation error and adjust the machine learning model, the models used for near-line simulation and the values of some of the input variables to improve simulation performance when the simulation error is larger than an error threshold.

29. The method of claim 28, wherein the method comprises operating the simulation engine for performing the off-line and near-line simulations before the next online simulation in order to provide the online simulator with an updated optimal operating point for online simulation.

30. A system for performing at least one of assessing, optimizing and/or controlling the performance of an Anaerobic Digestion (AD) plant, wherein the system comprises:
a user interface for allowing a user to enter user inputs to define various aspects of the AD plant operation and to view results of the simulation;
a database for storing inputs used for the simulation and/or optimization of the anaerobic digestion plant, the inputs including feedstock inputs, AD operational inputs, and simulation criteria; and
a server that controls the operation of the system and generates the user interface, the server being configured to operate a simulation engine according to an off-line simulation mode and a near-line simulation mode, wherein the simulation engine is configured to:
execute the offline simulation mode to perform a simulation using an Anaerobic Digestion (AD) operational model that includes several models for modelling several aspects of the AD plant operation and generating off-line simulator predictions of the AD plant operation for assessing the performance of the AD plant; and
execute the near-line simulation mode which uses the off-line simulator predictions for determining an optimal operating point based on at least one optimization goal and possible scenarios to optimize the performance of the AD plant,
wherein the simulation engine uses a sensitivity analysis and optimization model for performing optimization in the near-line simulation mode where the sensitivity analysis and optimization model includes a set of N input variables that have an influence for achieving the at least one optimization goal, an operating value for each input variable determined from the off-line simulation and a range over which the input variables are varied to define an N-dimensional mesh where the actual optimal operating point is a global maximum or a global minimum of the N-dimensional mesh corresponding to the at least one optimization goal.

31. A method for performing at least one of assessing, optimizing and/or controlling the performance of an Anaerobic Digestion (AD) plant, wherein the method comprises:
using a server to provide a user interface for allowing a user to enter user inputs to define various aspects of the AD plant operation and to view results of the simulation;
storing inputs in a database where the inputs are used for the simulation of the anaerobic digestion plant, the inputs including feedstock inputs, AD operational inputs, and simulation criteria; and
using the server to generate the user interface and operate a simulation engine according to a three stage process including an off-line simulation mode, a near-line simulation mode and an online simulation mode, where:
the offline simulation mode involves performing a simulation using an Anaerobic Digestion (AD) operational model that includes several models for modelling several aspects of the AD plant operation and generating off-line simulator predictions of the AD plant operation for assessing the performance of the AD plant;
the near-line simulation mode involves using the off-line simulator predictions for determining an optimal operating point based on at least one optimization goal and possible scenarios to optimize the performance of the AD plant, and performing a sensitivity analysis and using an optimization model during optimization during the near-line simulation mode where the sensitivity analysis and optimization model includes a set of N input variables that have an influence for achieving the at least one optimization goal, an operating value for each input variable determined from the off-line simulation and a range over which the input variables are varied to define an N-dimensional mesh where the actual optimal operating point is a global maximum or a global minimum of the N-dimensional mesh corresponding to the at least one optimization goal.

\* \* \* \* \*